US009932607B2

(12) United States Patent
Calos et al.

(10) Patent No.: US 9,932,607 B2
(45) Date of Patent: Apr. 3, 2018

(54) SITE-SPECIFIC INTEGRATION OF TRANSGENES INTO HUMAN CELLS

(71) Applicant: The Board of Trustees of the Leland Stanford Junior University, Palo Alto, CA (US)

(72) Inventors: Michele Pamela Calos, Menlo Park, CA (US); Ruby Yanru Tsai, San Jose, CA (US); Fangfang Zhu, Palo Alto, CA (US); Matthew Gamboa, Palo Alto, CA (US); Alfonso P. Farruggio, McAllen, TX (US); Simon Hippenmeyer, Menlo Park, CA (US); Bosiljka Tasic, Seattle, WA (US); Birgitt Schüle, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 268 days.

(21) Appl. No.: 14/539,909

(22) Filed: Nov. 12, 2014

(65) Prior Publication Data
US 2015/0140665 A1 May 21, 2015

Related U.S. Application Data

(60) Provisional application No. 61/904,867, filed on Nov. 15, 2013.

(51) Int. Cl.
C12N 15/90 (2006.01)
(52) U.S. Cl.
CPC .................. C12N 15/907 (2013.01)
(58) Field of Classification Search
None
See application file for complete search history.

(56) References Cited

U.S. PATENT DOCUMENTS

| | | | |
|---|---|---|---|
| 5,222,982 | A | 6/1993 | Ommaya |
| 5,385,582 | A | 1/1995 | Ommaya |
| 5,843,780 | A | 12/1998 | Thomson |
| 6,140,081 | A | 10/2000 | Barbas |
| 6,200,806 | B1 | 3/2001 | Thomson |
| 6,453,242 | B1 | 9/2002 | Eisenberg et al. |
| 6,534,261 | B1 | 3/2003 | Cox, III et al. |
| 7,029,913 | B2 | 4/2006 | Thomson |
| 7,153,684 | B1 | 12/2006 | Hogan |
| 7,888,121 | B2 | 2/2011 | Urnov et al. |
| 7,972,854 | B2 | 7/2011 | Miller et al. |
| 8,304,233 | B2 | 11/2012 | Calos |
| 8,420,395 | B2 | 4/2013 | Calos |
| 2007/0254842 | A1 | 11/2007 | Bankiewicz |
| 2008/0020465 | A1 | 1/2008 | Padidam |
| 2008/0081064 | A1 | 4/2008 | Jelle et al. |
| 2009/0047263 | A1 | 2/2009 | Yamanaka et al. |
| 2009/0068742 | A1 | 3/2009 | Yamanaka |
| 2009/0191159 | A1 | 7/2009 | Sakurada et al. |
| 2009/0196903 | A1 | 8/2009 | Kliman |
| 2009/0227032 | A1 | 9/2009 | Yamanaka et al. |
| 2009/0246875 | A1 | 10/2009 | Yamanaka et al. |
| 2009/0304646 | A1 | 12/2009 | Sakurada et al. |
| 2011/0136237 | A1 | 6/2011 | Ow et al. |
| 2012/0124686 | A1 | 5/2012 | Luo et al. |

FOREIGN PATENT DOCUMENTS

| | | |
|---|---|---|
| WO | 98/53058 | 11/1998 |
| WO | 98/53059 | 11/1998 |
| WO | 98/53060 | 11/1998 |
| WO | 02/16536 | 2/2002 |
| WO | 03/016496 | 2/2003 |

OTHER PUBLICATIONS

Yamaguchi et al. (PLoS ONE. Feb. 2011; 6(2): e17267, pp. 1-11).*
Tasic et al. (PNAS. May 10, 2011; 108(19): 7902-7907.*
Susan Mayor (BMJ. Dec. 4, 1999; vol. 319, p. 1453).*
Hockemeyer et al. (Nature Biotechnology. 2011; 29(8): 731-734)).*
Angel and Yanik (2010) "Innate Immune Suppression Enables Frequent Transfection with RNA Encoding Reprogramming Proteins" PLoS ONE 5(7):e11756.
Beumer et al. (2008) "Efficient gene targeting in *Drosophila* by direct embryo injection with zinc-finger nucleases" PNAS 105(50):19821-19826.
Boch et al. (2009) "Breaking the Code of DNA Binding Specificity of TAL-Type III Effectors" Science 326 (5959):1509-1512.
Byers et al. (2011) "SNCA Triplication Parkinson's Patient's iPSC-derived DA Neurons Accumulate α-Synuclein and Are Susceptible to Oxidative Stress" PLoS ONE 6(11):e26159.
Carey et al. (2009) "Reprogramming of murine and human somatic cells using a single polycistronic vector" Proc Natl Acad Sci USA 106(1):157-162.
Cermak et al. (2011) "Efficient design and assembly of custom TALEN and other TAL effector—based constructs for DNA targeting" Nucleic acids research 39:e82.
Chung et al. (2008) "Human Embryonic Stem Cell Lines Generated without Embryo Destruction" Cell Stem Cell 2(2)113-117.
Chung et al. (2009) "Wnt1-lmx1a Forms a Novel Autoregulatory Loop and Controls Midbrain Dopaminergic Differentiation Synergistically with the SHH-FoxA2 Pathway" Cell Stem Cell 5(6):646-658.
Chung et al. (2010) "The transcription factor orthodenticle homeobox 2 influences axonal projections and vulnerability of midbrain dopaminergic neurons" Brain 133:2022-2031.

(Continued)

*Primary Examiner* — Scott Long
(74) *Attorney, Agent, or Firm* — Edward J. Baba; Shweta Chandra; Bozicevic, Field & Francis LLP

(57) ABSTRACT

Methods for inserting a polynucleotide sequence into the genome of a human cell are provided. The present methods result in insertion of a polynucleotide sequence of interest into the H11 locus in the genome of a human cell. Also provided are nucleic acids that include sequences for integrating a polynucleotide sequence of interest into the H11 locus in the genome of a human cell. A transgenic human cell including site specific recombination sites at the H11 locus is also disclosed.

17 Claims, 11 Drawing Sheets

(56) References Cited

OTHER PUBLICATIONS

Doyle et al. (2012) "TAL Effector-Nucleotide Targeter (TALE-NT) 2.0: tools for TAL effector design and target prediction" Nucleic Acids Res 40(W1):W117-W122.
Farruggio et al. (2012) "Efficient reversal of phiC31 integrase recombination in mammalian cells" Biotechnol J 7(11):1332-1336.
Friling et al. (2009) "Efficient production of mesencephalic dopamine neurons by Lmx1a expression in embryonic stem cells" PNAS 106(18):7613-7618.
Grindley et al. (2006) "Mechanisms of Site-Specific Recombination" Annu Rev Biochem 75:567-605.
Hippenmeyer et al. (2010) "Genetic Mosaic Dissection of Lis1 and Ndel1 in Neuronal Migration" Neuron 68(4):695-709.
Hockemeyer et al. (2011) "Genetic engineering of human pluripotent cells using TALE nucleases" Nat Biotechnol 29:731-734.
Keravala et al. (2006) "A diversity of serine phage integrases mediate site-specific recombination in mammalian cells" Mol Genet Genomics 276(2):135-146.
Koshimizu et al. (1996) "Functional requirement of gp130-mediated signaling for growth and survival of mouse primordial germ cells in vitro and derivation of embryonic germ (EG) cells" Development 122:1235-1242.
Lin et al. (2009) "Foxa1 and Foxa2 function both upstream of and cooperatively with Lmx1a and Lmx1b in a feedforward loop promoting mesodiencephalic dopaminergic neuron development" Dev Biol 333(2):386-396.
Matsui et al. (1992) "Derivation of pluripotential embryonic stem cells from murine primordial germ cells in culture" Cell 70(5):841-847.
Okada et al. (1999) "Imaging Cells in the Developing Nervous System with Retrovirus Expressing Modified Green Fluorescent Protein" Exp Neurol 156(2):394-406.
Russell et al. (2006) "Phage Bxb1 integrase mediates highly efficient site-specific recombination in mammalian cells" Biotechniques 40(4):460-464.
Shamblott et al. (1998) "Derivation of pluripotent stem cells from cultured human primordial germ cells" PNAS 95(23):13726-13731.
Shamblott et al. (2001) "Human embryonic germ cell derivatives express a broad range of developmentally distinct markers and proliferate extensively in vitro" PNAS 98(1):113-118.
Suzuki et al. (2014) "A Novel System for Simultaneous or Sequential Integration of Multiple Gene-Loading Vectors into a Defined Site of a Human Artificial Chromosome" PLoS ONE 9(10):e110404 (1-9).
Szymczak et al. (2004) "Correction of multi-gene deficiency in vivo using a single 'self-cleaving' 2A peptide-based retroviral vector" Nat Biotechnol 22:589-594.
Tasic et al. (2011) "Site-specific integrase-mediated transgenesis in mice via pronuclear injection" PNAS 108(19):7902-7907.
Tasic et al. (2012) "Extensions of MADM (Mosaic Analysis with Double Markers) in Mice" PLoS One 7(3):e33332.
Zhu et al. (2014) "DICE, an efficient system for iterative genomic editing in human pluripotent stem cells" Nucl Acids Res ePub 42(5):e34(1-13).

* cited by examiner

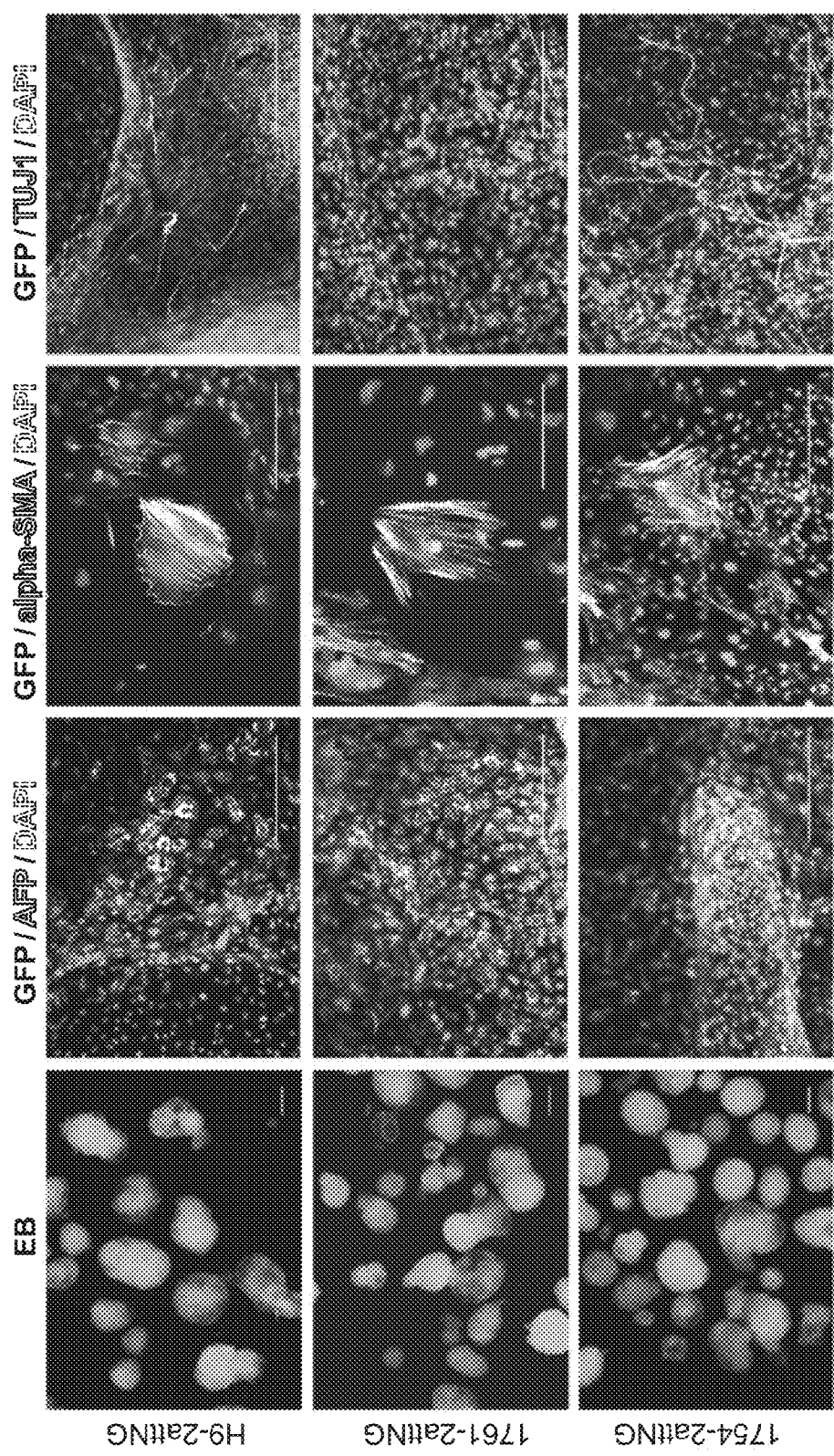

SEQUENCE LISTING

<160> NUMBER OF SEQ ID NOS: 20

<210> SEQ ID NO 1
<211> LENGTH: 58
<212> TYPE: DNA
<213> ORGANISM: Homo sapiens

<400> SEQUENCE: 1
tatagatatc ctggtattag ccacaaggct atgctatcta tagggtcagt ccagtata    58

<210> SEQ ID NO 2
<211> LENGTH: 57
<212> TYPE: DNA
<213> ORGANISM: Artificial sequence
<220> FEATURE:
<223> OTHER INFORMATION: synthetic polynucleotide

<400> SEQUENCE: 2
atcggcggcc gcggcgcgcc ccttttttcct tgagctttaa agaccccaac aggtcag    57

<210> SEQ ID NO 3
<211> LENGTH: 41
<212> TYPE: DNA
<213> ORGANISM: Artificial sequence
<220> FEATURE:
<223> OTHER INFORMATION: synthetic polynucleotide

<400> SEQUENCE: 3
atcggtcgac gctcttggga agaagtcaaa cattatttca g    41

<210> SEQ ID NO 4
<211> LENGTH: 69
<212> TYPE: DNA
<213> ORGANISM: Artificial sequence
<220> FEATURE:
<223> OTHER INFORMATION: synthetic polynucleotide

<400> SEQUENCE: 4
atcggtcgac ggcgcgccat ttaaatgttt aaacccatag ttgatttctc ctaaatcaag    60
atagagtcc    69

<210> SEQ ID NO 5
<211> LENGTH: 57
<212> TYPE: DNA
<213> ORGANISM: Artificial sequence
<220> FEATURE:
<223> OTHER INFORMATION: synthetic polynucleotide

<400> SEQUENCE: 5
atcggcggcc gcccgcggtt aattaaccaa atgattaatc ctgatggctg aggagac    57

<210> SEQ ID NO 6
<211> LENGTH: 32
<212> TYPE: DNA
<213> ORGANISM: Artificial sequence
<220> FEATURE:
<223> OTHER INFORMATION: synthetic polynucleotide

<400> SEQUENCE: 6
aattatttaa atgactcaga actgtactgt at    32

<210> SEQ ID NO 7
<211> LENGTH: 30
<212> TYPE: DNA
<213> ORGANISM: Artificial sequence

```
<220> FEATURE:
<223> OTHER INFORMATION: synthetic polynucleotide

<400> SEQUENCE: 7
aattagatct ccttttcct tgagctttaa                                          30

<210> SEQ ID NO 8
<211> LENGTH: 24
<212> TYPE: DNA
<213> ORGANISM: Artificial sequence
<220> FEATURE:
<223> OTHER INFORMATION: synthetic polynucleotide

<400> SEQUENCE: 8
aattccatag ttgatttctc ctaa                                               24

<210> SEQ ID NO 9
<211> LENGTH: 32
<212> TYPE: DNA
<213> ORGANISM: Artificial sequence
<220> FEATURE:
<223> OTHER INFORMATION: synthetic polynucleotide

<400> SEQUENCE: 9
aattggcgcg ccagtatgtt cctttaagga ag                                      32

<210> SEQ ID NO 10
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 10
acccagtccg ccctgagcaa                                                    20

<210> SEQ ID NO 11
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 11
tgggcagaag ggagggtatg gacatgtaag                                         30

<210> SEQ ID NO 12
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 12
agttccaggc ttatagtcat tattccctaa                                         30

<210> SEQ ID NO 13
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 13
gtctcatgag cggatacata tttgaatgta                                         30
```

```
<210> SEQ ID NO 14
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 14
gacggcgacg taaacggcca                                               20

<210> SEQ ID NO 15
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 15
ttgctcaggg cggactgggt                                               20

<210> SEQ ID NO 16
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 16
ccaaccacct tgacctttac ctcattatct                                    30

<210> SEQ ID NO 17
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 17
ctgcagtcca gcctggcgac                                               20

<210> SEQ ID NO 18
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 18
acggcggtct ccgtcgtcag                                               20

<210> SEQ ID NO 19
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 19
aagctgagga atcacatgga gtgaatagca                                    30

<210> SEQ ID NO 20
<211> LENGTH: 20
<212> TYPE: DNA
```

```
<213> ORGANISM: Artificial sequence
<220> FEATURE:
<223> OTHER INFORMATION: synthetic polynucleotide

<400> SEQUENCE: 20
gggtggggca ggacagcaag                                              20
```

SITE-SPECIFIC INTEGRATION OF TRANSGENES INTO HUMAN CELLS

CROSS-REFERENCE TO RELATED APPLICATIONS

Pursuant to 35 U.S.C. § 119 (e), this application claims priority to the filing date of U.S. Provisional Patent Application Ser. No. 61/904,867 filed on Nov. 15, 2013; the disclosure of which applications are herein incorporated by reference.

INTRODUCTION

Human cells offer tremendous potential for understanding human development and disease mechanism as well as for use in drug screening and cell therapy. In many instances, it is desirable to insert a nucleic acid sequence into the human genome such that the inserted nucleic acid may be expressed while causing no disruption of the regulatory elements or genes in the genome at or near the insertion site.

However, the currently available technologies for inserting a transgene into the human genome have serious drawbacks. New methods for inserting genes into a human cell in a site specific manner are needed since the current technologies have serious drawbacks. For example, gene insertion mediated by retroviruses, lentiviruses, transposons, and non-homologous end joining results in random integration. The consequent lack of control over transgene insertion site, copy number, and orientation compromises the precision of experiments. Moreover, these methods often have limits on the size of the DNA that can be inserted.

The methods, nucleic acids, and human transgenic cells disclosed herein address the above limitations and fulfill other needs.

SUMMARY

Methods for inserting a polynucleotide sequence into the genome of a human cell are provided. The present methods result in insertion of a polynucleotide sequence of interest into the H11 locus in the genome of a human cell. Also provided are nucleic acids that include sequences for integrating a polynucleotide sequence of interest into the H11 locus in the genome of a human cell. A transgenic human cell including site specific recombination sites at the H11 locus is also disclosed.

A method of inserting a polynucleotide sequence into a genome of a human cell is provided. The method includes introducing into the human cell: a circular nucleic acid comprising the polynucleotide sequence flanked by a phiC31 first recombination site and a Bxb1 first recombination site; a phiC31 integrase; and a Bxb1 integrase, wherein the human cell comprises a phiC31 second recombination site and a Bxb1 second recombination site at H11 locus in chromosome 22; maintaining the human cell under conditions that facilitate recombination between phiC31 first recombination and phiC31 second recombination sites and between the Bxb1 first recombination and Bxb1 second recombination sites, wherein the introducing and maintaining results in insertion of the polynucleotide sequence into the genome of the human cell at the H11 locus.

In certain embodiments, the method of inserting the polynucleotide sequence into a genome of a human cell may include inserting the phiC31 second recombination site and the Bxb1 second recombination site at the H11 locus prior to introducing the circular nucleic acid, and the phiC31 and Bxb1 integrases, wherein the inserting includes introducing into the human cell, a circular nucleic acid comprising the phiC31 second recombination site and the Bxb1 second recombination site flanked by a first sequence homologous to a first region of the H11 locus and a second sequence homologous to a second region of the H11 locus; and maintaining the human cell under conditions that facilitate recombination between the first sequence and the first region and between the second sequence and the second region, wherein the introducing and maintaining results in insertion of the phiC31 second recombination site and the Bxb1 second recombination site at the H11 locus.

In certain embodiments, the phiC31 first recombination site may be attB and the phiC31 second recombination site may be attP.

In other embodiments, the phiC31 first recombination site may be attP and the phiC31 second recombination site may be attB.

In certain embodiments, the Bxb1 first recombination site may be attB and the Bxb1 second recombination site may be attP.

In other embodiments, the Bxb1 first recombination site may be attP and the Bxb1 second recombination site may be attB.

In certain embodiments, the phiC31 and Bxb1 integrases may be introduced into the human cell by introducing a nucleic acid encoding the phiC31 and Bxb1 integrases into the cell. The nucleic acid encoding the phiC31 and/or Bxb1 integrases may be an mRNA or a circular DNA.

In certain embodiments, phiC31 and Bxb1 integrases are introduced into the human cell by introducing a first nucleic acid encoding the phiC31 integrase and a second nucleic acid encoding the Bxb1 integrase. In certain cases, the first and second nucleic acids may be a mRNA. In other cases, the first and second nucleic acids may be a circular DNA.

In exemplary embodiments, the polynucleotide sequence being inserted into the genome may encode a polypeptide, for example, a transcription factor.

Exemplary human cells include pluripotent stem (PS) cells, such as, embryonic stem (ES) cells and induced pluripotent stem (iPS) cells.

BRIEF DESCRIPTION OF THE DRAWINGS

The accompanying drawings, which are incorporated herein, form part of the specification. Together with this written description, the drawings further serve to explain the principles of, and to enable a person skilled in the relevant art(s), to make and use the present invention.

FIGS. 6A-6C illustrate pluripotency of recipient ESC and iPSC lines.

DEFINITIONS

Figure 1A:
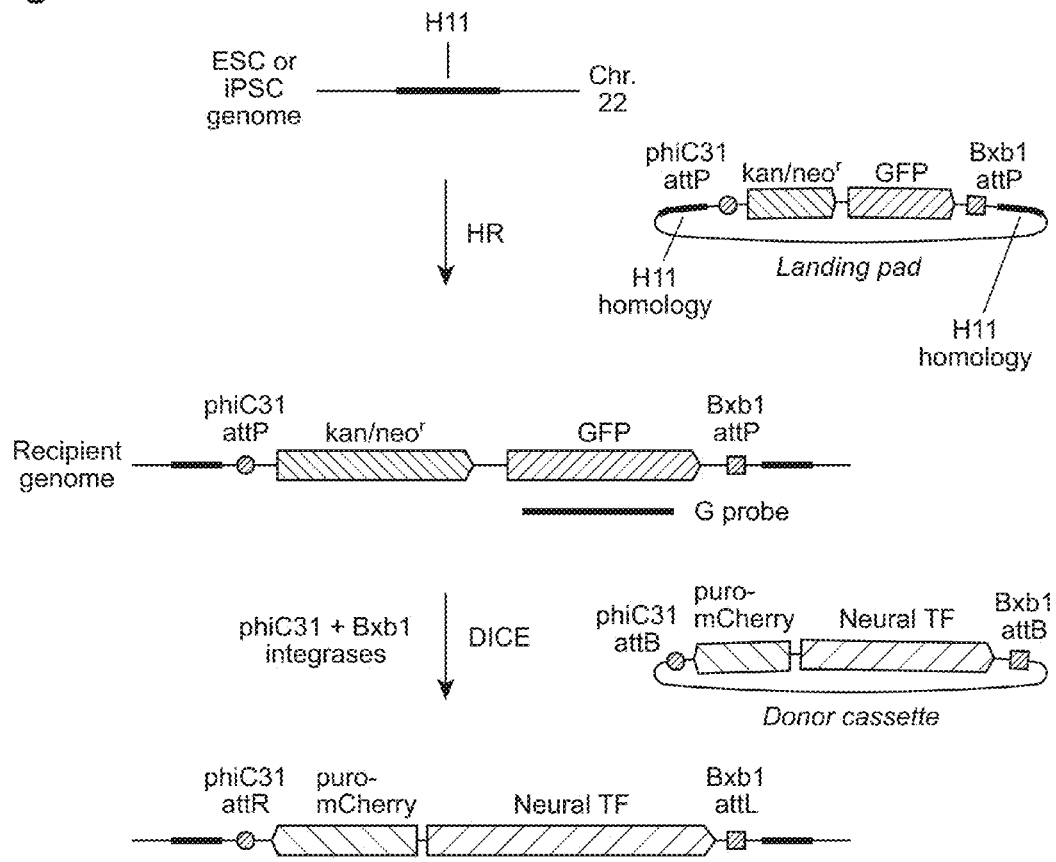
FIGS. 1A-1B illustrate dual integrase cassette exchange (DICE) strategy (FIG. 1A) and H11 location (FIG. 1B).

As used herein, "locus" refers to a specific location on a chromosome. A known locus can contain known genetic information, such as one or more polymorphic marker sites.

By "nucleic acid construct" it is meant a nucleic acid sequence that has been constructed to comprise one or more functional units not found together in nature. Examples include circular, double-stranded, extrachromosomal DNA molecules (plasmids), cosmids (plasmids containing COS sequences from lambda phage), viral genomes comprising non-native nucleic acid sequences, and the like.

As used herein, "nucleic acid fragment of interest" or "polynucleotide sequence of interest" refers to any nucleic acid fragment that one wishes to insert into a genome. Examples of nucleic acid fragments of interest include any genes (e.g., RNA encoding, protein-encoding), such as therapeutic genes, marker genes, control regions, trait-producing fragments, and the like.

A "coding sequence" or a sequence which "encodes" a selected polypeptide, is a nucleic acid molecule which is transcribed (in the case of DNA) and translated (in the case of mRNA) into a polypeptide, for example, in vivo when placed under the control of appropriate regulatory sequences (or "control elements"). The boundaries of the coding sequence are typically determined by a start codon at the 5' (amino) terminus and a translation stop codon at the 3' (carboxy) terminus. A coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence. Other "control elements" such a regulatory sequences, e.g., promoter sequences may also be associated with a coding sequence.

"Operably-linked" refers to the association of nucleic acid sequences on a single nucleic acid fragment so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or anti-sense orientation.

"Homozygous" state means a genetic condition existing when identical alleles reside at corresponding loci on homologous chromosomes. In contrast, "heterozygous" state means a genetic condition existing when different alleles reside at corresponding loci on homologous chromosomes.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

An "expression cassette" comprises any nucleic acid construct capable of directing the expression of a gene/coding sequence of interest. Such cassettes can be constructed into a "vector," "vector construct," "expression vector," or "gene transfer vector," in order to transfer the expression cassette into target cells. Thus, the term includes cloning and expression vehicles, as well as viral vectors.

A cell has been "transformed" or "transfected" by exogenous or heterologous DNA, e.g. a DNA construct, when such DNA has been introduced inside the cell. The transforming DNA may or may not be integrated (covalently linked) into the genome of the cell.

By "recombination" it is meant a process of exchange of genetic information between two polynucleotides. As used herein, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and leads to the transfer of genetic information from the donor to the target. Homologous recombination may result in an alteration of the sequence of the target molecule, if the donor polynucleotide differs from the target molecule and part or all of the sequence of the donor polynucleotide is incorporated into the target polynucleotide.

By "integration" it is meant that the gene of interest is stably inserted into the cellular genome, i.e., covalently linked to the nucleic acid sequence within the cell's chromosomal DNA. By "targeted integration" it is meant that the gene of interest is inserted into the cell's chromosomal or mitochondrial DNA at a specific site, or "integration site".

A "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e. a polypeptide found in nature) or fragment thereof; a variant polypeptide (i.e. a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, a "target locus" is a region of DNA into which a gene or polynucleotide of interest is integrated, e.g., a region of chromosomal or mitochondrial DNA in a cell.

As used herein, the term "reporter gene" refers to a coding sequence whose product may be assayed easily and quantifiably when attached to promoter and in some instances enhancer elements and introduced into tissues or cells. The promoter may be a constitutively active promoter or it may be an inducible promoter.

By "targeted nuclease" it is meant a nuclease that is targeted to a specific DNA sequence. Targeted nucleases are targeted to a specific DNA sequence by the DNA binding domain to which they are fused. In other words, the nuclease is guided to a DNA sequence, e.g. a chromosomal sequence or an extrachromosomal sequence, e.g. an episomal sequence, a minicircle sequence, a mitochondrial sequence, a chloroplast sequence, etc., by virtue of its fusion to a DNA binding domain with specificity for the target DNA sequence of the target locus of interest.

By "pluripotent stem cell" or "pluripotent cell" it is meant a cell that has the ability under appropriate conditions of producing progeny of several different cell types that are derivatives of all of the three germinal layers (endoderm, mesoderm, and ectoderm). Pluripotent stem cells are capable of forming teratomas. Examples of pluripotent stem cells are embryonic stem (ES) cells, embryonic germ stem (EG) cells, and induced pluripotent stem (iPS) cells. PS cells may be from any organism of interest, including, e.g., human.

By "embryonic stem cell" or "ES cell" it is meant a cell that a) can self-renew, b) can differentiate to produce all types of cells in an organism, and c) is derived from a developing organism or is an established ES cell line which was derived from a developing organism. ES cell may be derived from the inner cell mass of the blastula of a developing organism. ES cell may be derived from a blastomere generated by single blastomere biopsy (SBB) involving removal of a single blastomere from the eight cell stage of a developing organism. In general, SBB provides a non-destructive alternative to inner cell mass isolation. SBB and generation of hES cells from the biopsied blastomere is described in Cell Stem Cell, 2008 Feb. 7; 2(2):113-7. ES cells can be cultured over a long period of time while maintaining the ability to differentiate into all types of cells in an organism. In culture, ES cells typically grow as flat colonies with large nucleo-cytoplasmic ratios, defined borders and prominent nuclei. In addition, ES cells express SSEA-3, SSEA-4, TRA-1-60, TRA-1-81, and Alkaline Phosphatase, but not SSEA-1. Examples of methods of generating and characterizing ES cells may be found in, for example, U.S. Pat. No. 7,029,913, U.S. Pat. No. 5,843,780, and U.S. Pat. No. 6,200,806, the disclosures of which are incorporated herein by reference.

By "embryonic germ stem cell", embryonic germ cell" or "EG cell" it is meant a cell that a) can self-renew, b) can differentiate to produce all types of cells in an organism, and c) is derived from germ cells and germ cell progenitors, e.g. primordial germ cells, i.e. those that would become sperm and eggs. Embryonic germ cells (EG cells) are thought to have properties similar to embryonic stem cells as described above. Examples of methods of generating and characterizing EG cells may be found in, for example, U.S. Pat. No. 7,153,684; Matsui, Y., et al., (1992) Cell 70:841; Shamblott, M., et al. (2001) Proc. Natl. Acad. Sci. USA 98: 113; Shamblott, M., et al. (1998) Proc. Natl. Acad. Sci. USA, 95:13726; and Koshimizu, U., et al. (1996) Development, 122:1235, the disclosures of which are incorporated herein by reference.

By "induced pluripotent stem cell" or "iPS cell" it is meant a cell that a) can self-renew, b) can differentiate to produce all types of cells in an organism, and c) is derived from a somatic cell. iPS cells have an ES cell-like morphology, growing as flat colonies with large nucleo-cytoplasmic ratios, defined borders and prominent nuclei. In addition, iPS cells express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. iPS cells may be generated by providing the cell with "reprogramming factors", i.e., one or more, e.g., a cocktail, of biologically active factors that act on a cell to alter transcription, thereby reprogramming a cell to pluripotency. Examples of methods of generating and characterizing iPS cells may be found in, for example, Application Nos. US20090047263, US20090068742, US20090191159, US20090227032, US20090246875, and US20090304646, the disclosures of which are incorporated herein by reference.

By "somatic cell" it is meant any cell in an organism that, in the absence of experimental manipulation, does not ordinarily give rise to all types of cells in an organism. In other words, somatic cells are cells that have differentiated sufficiently that they will not naturally generate cells of all three germ layers of the body, i.e., ectoderm, mesoderm and endoderm. For example, somatic cells would include both neurons and neural progenitors, the latter of which may be able to self-renew and naturally give rise to all or some cell types of the central nervous system but cannot give rise to cells of the mesoderm or endoderm lineages.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a human cell" includes a plurality of such human cells and reference to "the polynucleotide sequence of interest" includes reference to one or more polynucleotide sequences of interest and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Methods for inserting a polynucleotide sequence into the genome of a human cell are provided. The present methods result in insertion of a polynucleotide sequence of interest into the H11 locus in the genome of a human cell. Also provided are nucleic acids that include sequences for integrating a polynucleotide sequence of interest into the H11 locus in the genome of a human cell. A transgenic human cell including site specific recombination sites at the H11 locus is also disclosed.

Method for Inserting a Polynucleotide Sequence into a Genome of a Human Cell

In certain embodiments, the method includes inserting a polynucleotide sequence of interest into a genome of a human cell.

The method of inserting a polynucleotide sequence into a genome of a human cell may include: introducing into the human cell a circular nucleic acid comprising the polynucleotide sequence flanked by a phiC31 first recombination site and a Bxb1 first recombination site; a phiC31 integrase; and a Bxb1 integrase, where the human cell comprises a phiC31 second recombination site and a Bxb1 second recombination site at H11 locus in chromosome 22; and maintaining the human cell under conditions that facilitate recombination between phiC31 first recombination and phiC31 second recombination sites and between the Bxb1 first recombination and Bxb1 second recombination sites, where the introducing and maintaining results in insertion of the polynucleotide sequence into the genome of the human cell at the H11 locus.

In certain embodiments, the method may include inserting the phiC31 second recombination site and the Bxb1 second recombination site at the H11 locus prior to introducing the circular nucleic acid, and the phiC31 and Bxb1 integrases, where the inserting includes introducing into the human cell, a circular nucleic acid comprising the phiC31 second recombination site and the Bxb1 second recombination site flanked by a first sequence homologous to a first region of the H11 locus and a second sequence homologous to a second region of the H11 locus; and maintaining the human cell under conditions that facilitate recombination between the first sequence and the first region and between the second sequence and the second region, wherein the introducing and maintaining results in insertion of the phiC31 second recombination site and the Bxb1 second recombination site at the H11 locus.

In another embodiment, the method for inserting a polynucleotide of interest into a human cell may include introducing a first circular nucleic acid comprising a phiC31 second recombination site and the Bxb1 second recombination site flanked by a first sequence homologous to a first region of the H11 locus and a second sequence homologous to a second region of the H11 locus; and maintaining the human cell under conditions that facilitate recombination between the first sequence and the first region and between the second sequence and the second region, wherein the introducing and maintaining results in insertion of the phiC31 second recombination site and the Bxb1 second recombination site at the H11 locus. The method may further include introducing into the human cell comprising the phiC31 second recombination site and the Bxb1 second recombination site at the H11 locus a second circular nucleic acid comprising the polynucleotide sequence of interest flanked by a phiC31 first recombination site and a Bxb1 first recombination site; a phiC31 integrase; and a Bxb1 integrase and maintaining the human cell under conditions that facilitate recombination between phiC31 second recombination and phiC31 first recombination sites and between the Bxb1 second recombination and Bxb1 first recombination sites, wherein the introducing and maintaining results in insertion of the polynucleotide sequence into the genome of the human cell at the H11 locus.

As used herein a "recombination site" or "recognition site" is a DNA sequence that serves a substrate for a recombinase so as to provide for unidirectional site-specific recombination. In general, the recombinases used in the invention involve two recognition sites, one that is positioned in the integration site (the site into which a nucleic acid is to be integrated) and another adjacent a nucleic acid of interest to be introduced into the integration site. The terms "recombinase" and "integrase" are used interchangeably herein.

As used herein, a phiC31 first recombination site and a phiC31 second recombination site refers to nucleic acid sequences that are recognized by the phiC31 integrase and used as a substrates for recombination between the nucleic acid sequences. In certain cases, the phiC31 first recombination site may be phiC31 attB and the phiC31 second recombination site may be phiC31 attP. In other cases, the phiC31 first recombination site may be phiC31 attP and the phiC31 second recombination site may be phiC31 attB. phiC31 attP and phiC31 attB are DNA sequences specifically recognized by phiC31 integrase.

As used herein, a Bxb1 first recombination site and a Bxb1 second recombination site refers to recognition sequences that are recognized by the Bxb1 integrase and used as a substrates for recombination between the recognition sequences. In certain cases, the Bxb1 first recombination site may be Bxb1 attB and the Bxb1 second recombination site may be Bxb1 attP. In other cases, the Bxb1 first recombination site may be Bxb1 attP and the Bxb1 second recombination site may be Bxb1 attB. Bxb1 attP and Bxb1 attB are DNA sequences specifically recognized by Bxb1 integrase.

In certain embodiments, when the phiC31 second recombination site is attP, the Bxb1 second recombination site may be attP and the phiC31 first recombination site may be attB and the Bxb1 first recombination site may be attB.

In other embodiments, when the phiC31 second recombination site is attB, the Bxb1 second recombination site may be attB and the phiC31 first recombination site may be attP and the Bxb1 first recombination site may be attP.

AttB and attP sites are general names for the recombination site pairs that are recognized by and recombined by bacteriophage integrases, such as, phiC31 and Bx1. In general, the sequence of attB and attP sites are different from each other and further the sequences of attB and attP sites pairs that recognized and recombined by different integrases are different.

As used herein, the first recombination site may be present adjacent to the polynucleotide sequence of interest and the second recombination site may be inserted into the genome of the human cell at the H11 locus.

In certain embodiments, the method includes introducing into the human cell a circular nucleic acid that includes the polynucleotide sequence flanked by a phiC31 attB site nucleic acid sequence and a Bxb1 attB site; a phiC31 integrase; and a Bxb1 integrase. In general, the human cell includes a phiC31 attP site and a Bxb1 attP site at H11 locus in chromosome 22. The method further includes maintaining the human cell under conditions that facilitate recombination between phiC31 attB and phiC31 attP sites and between the Bxb1 attB and Bxb1 attP sites, wherein the introducing and maintaining results in insertion of the polynucleotide sequence into the genome of the human cell at the H11 locus.

In certain embodiments, the method may include inserting the phiC31 attP site and the Bxb1 attP site at the H11 locus prior to introducing the circular nucleic acid, and the phiC31 and Bxb1 integrases. In certain cases, the inserting may be carried out by introducing into the human cell, a circular nucleic acid comprising the phiC31 attP site and the Bxb1 attP site flanked by a first sequence homologous to a first region of the H11 locus and a second sequence homologous to a second region of the H11 locus; and maintaining the human cell under conditions that facilitate recombination between the first sequence and the first region and between the second sequence and the second region, wherein the introducing and maintaining results in insertion of the phiC31 attP site and the Bxb1 attP site at the H11 locus.

In certain embodiments, the method for inserting a polynucleotide of interest into a human cell may include introducing a first circular nucleic acid comprising a phiC31 attP site and the Bxb1 attP site flanked by a first sequence homologous to a first region of the H11 locus and a second sequence homologous to a second region of the H11 locus; and maintaining the human cell under conditions that facilitate recombination between the first sequence and the first region and between the second sequence and the second region, wherein the introducing and maintaining results in insertion of the phiC31 attP site and the Bxb1 attP site at the H11 locus. The method may further include inserting into the human cell comprising the phiC31 attP site and the Bxb1 attP site at the H11 locus a second circular nucleic acid comprising the polynucleotide sequence of interest flanked by a phiC31 attB site and a Bxb1 attB site; a phiC31 integrase; and a Bxb1 integrase and maintaining the human cell under conditions that facilitate recombination between phiC31 attB and phiC31 attP sites and between the Bxb1 attB and Bxb1 attP sites, wherein the introducing and maintaining results in insertion of the polynucleotide sequence into the genome of the human cell at the H11 locus.

In certain cases, the introducing the first circular nucleic acid comprising a phiC31 second recombination site and the Bxb1 second recombination site flanked by a first sequence homologous to a first region of the H11 locus and a second sequence homologous to a second region of the H11 locus may result in insertion of the phiC31 second recombination site and the Bxb1 second recombination site at the H11 locus by spontaneous homologous recombination. In other words, the phiC31 second recombination site and the Bxb1 second recombination site may be introduced into the H11 locus via spontaneous homologous recombination. As noted above, the phiC31 second recombination site may be attP while the Bxb1 second recombination site may be attB, for example.

In certain cases, the insertion of the phiC31 second recombination site and the Bxb1 second recombination site at the H11 locus may be carried out by a "targeted nuclease". By a "targeted nuclease" it is meant a nuclease that cleaves a specific DNA sequence to produce a double strand break at that sequence. In these aspects of the method, this cleavage site becomes the site of integration for the phiC31 second recombination site and the Bxb1 second recombination site. As used herein, a nuclease includes naturally occurring nucleases as well as recombinant, i.e. engineered nucleases, such as, variant nucleases that are based on the sequence of the naturally occurring nuclease but include modifications, such as, fusion to a heterologous protein, mutations, and the like.

One example of a targeted nuclease that may be used in the subject methods is a TAL Nuclease ("TALN", TAL effector nuclease, or "TALEN"). A TALN is a targeted nuclease comprising a nuclease fused to a TAL effector DNA binding domain. By "transcription activator-like effector DNA binding domain", "TAL effector DNA binding domain", or "TALE DNA binding domain" it is meant the polypeptide domain of TAL effector proteins that is responsible for binding of the TAL effector protein to DNA. TAL effector proteins are secreted by plant pathogens of the genus *Xanthomonas* during infection. These proteins enter the nucleus of the plant cell, bind effector-specific DNA sequences via their DNA binding domain, and activate gene transcription at these sequences via their transactivation domains. TAL effector DNA binding domain specificity depends on an effector-variable number of imperfect 34 amino acid repeats, which comprise polymorphisms at select repeat positions called repeat variable-diresidues (RVD). TALENs are described in greater detail in US Patent Application No. 2011/0145940, which is herein incorporated by reference. The most recognized example of a TALEN in the art is a fusion polypeptide of the FokI nuclease to a TAL effector DNA binding domain.

Another example of a targeted nuclease that finds use in the subject methods is a zinc finger nuclease or "ZFN". ZFNs are targeted nucleases comprising a nuclease fused to a zinc finger DNA binding domain. By a "zinc finger DNA binding domain" or "ZFBD" it is meant a polypeptide domain that binds DNA in a sequence-specific manner through one or more zinc fingers. A zinc finger is a domain of about 30 amino acids within the zinc finger binding domain whose structure is stabilized through coordination of a zinc ion. Examples of zinc fingers include $C_2H_2$ zinc fingers, $C_3H$ zinc fingers, and $C_4$ zinc fingers. A "designed" zinc finger domain is a domain not occurring in nature whose design/composition results principally from rational criteria, e.g., application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496. A "selected" zinc finger domain is a domain not found in nature whose production results primarily from an empirical process such as phage display, interaction trap or hybrid selection. ZFNs are described in greater detail in U.S. Pat. No. 7,888,121 and U.S. Pat. No. 7,972,854, the complete disclosures of which are incorporated herein by reference. The most recognized example of a ZFN in the art is a fusion of the FokI nuclease with a zinc finger DNA binding domain.

Another example of a targeted nuclease that finds use in the subject methods is a targeted Spo11 nuclease, a polypeptide comprising a Spo11 polypeptide having nuclease activity fused to a DNA binding domain, e.g. a zinc finger DNA binding domain, a TAL effector DNA binding domain, etc. that has specificity for a DNA sequence of interest. See, for example, U.S. Application No. 61/555,857, the disclosure of which is incorporated herein by reference.

Other non-limiting examples of targeted nucleases include naturally occurring and recombinant nucleases, e.g. CRISPR/Cas9, restriction endonucleases, meganucleases homing endonucleases, and the like.

Typically, targeted nucleases are used in pairs, with one targeted nuclease specific for one sequence of an integration site and the second targeted nuclease specific for a second sequence of an integration site. In the methods presented herein, any targeted nuclease(s) that are specific for the integration site of interest and promote the cleavage of an integration site may be used. The targeted nuclease(s) may be stably expressed by the cells. Alternatively, the targeted nuclease(s) may be transiently expressed by the cells, e.g. it may be provided to the cells prior to, simultaneously with, or subsequent to contacting the cells with the landing pad generating polynucleotide. If transiently expressed by the cells, the targeted nuclease(s) may be provided to cells as DNA, e.g. plasmid or vector, as described herein, e.g., by using transfection, nucleofection, or the like. Alternatively, targeted nuclease(s) may be provided to cells as mRNA encoding the targeted nuclease(s), e.g. using well-developed transfection techniques; see, e.g. Angel and Yanik (2010) PLoS ONE 5(7): e11756; Beumer et al. (2008) PNAS 105(50):19821-19826, and the commercially available TransMessenger® reagents from Qiagen, Stemfect™ RNA Transfection Kit from Stemgent, and TransIT®-mRNA Transfection Kit from Mirus Bio LLC. Alternatively, the targeted nuclease(s) may be provided to cells as a polypeptide. Such polypeptides may optionally be fused to a polypeptide domain that increases solubility of the product, and/or fused to a polypeptide permeant domain to promote uptake by the cell. The targeted nuclease(s) may be produced by eukaryotic cells or by prokaryotic cells, it may be further processed by unfolding, e.g. heat denaturation, DTT reduction, etc. and may be further refolded, using methods known in the art. It may be modified, e.g. by chemical derivatization or by molecular biology techniques and synthetic chemistry, e.g. to so as to improve resistance to proteolytic degradation or to optimize solubility properties or to render the polypeptide more suitable as a therapeutic agent.

In certain cases, the step of introducing a nucleic acid into the human cell may be carried out by any method known in the art. For example, a nucleic acid may be introduced into a human cell by injection (into the nucleus or cytoplasm), transfection, viral infection, nucleofection, electroporation, calcium chloride transfection, and lipofection, and the like. Nucleic acid can be introduced as naked nucleic acid, as nucleic acid complexed with an agent such as a liposome or a stabilizing agent and the like.

In certain cases, the phiC31 and Bxb1 integrases may be transiently expressed in the human cell into which the polynucleotide sequence of interest has been introduced. The transient expression may result in irreversible recombination between cognate attP and attB sites, resulting in precise integration of the polynucleotide sequence of interest.

In certain cases, the phiC31 and Bxb1 integrases and the circular nucleic acid containing the polynucleotide of interest flanked by the phiC31 first recombination and Bxb1 first recombination sites may be introduced into the human cell simultaneously or sequentially. In certain cases, the circular nucleic acid containing the polynucleotide of interest flanked by the phiC31 first recombination and Bxb1 first recombination sites may be introduced into the human cell followed by introduction of the phiC31 and Bxb1 integrases or vice versa.

In certain cases, the phiC31 and Bxb1 integrases may be introduced into the human cell by introducing a nucleic acid encoding the phiC31 and Bxb1 integrases into the cell. A single nucleic acid may encode both the phiC31 and Bxb1 integrases. In certain cases, a first nucleic acid may encode the phiC31 integrase and a second nucleic acid may encode the Bxb1 integrase. In certain cases, the phiC31 and Bxb1 integrases may be introduced into the human cell simultaneously.

In certain cases, the phiC31 and Bxb1 integrases may be introduced into the human cell by introducing a nucleic acid encoding the phiC31 and Bxb1 integrases into the cell, wherein the nucleic acid is an mRNA or a DNA, e.g., a circular DNA. In certain cases, a nucleic acid encoding the phiC31 integrase may be a circular DNA while a nucleic acid encoding the Bxb1 integrase may be a mRNA or vice versa.

In certain cases, the circular nucleic acid comprising the phiC31 second recombination site and the Bxb1 second recombination site flanked by a first sequence homologous to a first region of the H11 locus and a second sequence homologous to a second region of the H11 locus may be referred to as a landing pad generating construct. In addition to the phiC31 second recombination site and the Bxb1 second recombination site flanked by a first sequence homologous to a first region of the H11 locus and a second sequence homologous to a second region of the H11 locus, the landing pad generating construct may include a reporter gene, a selection marker, or both. In certain cases, the landing pad generating construct may include a landing pad cassette comprising from 5' to 3' direction: a first sequence homologous to a first region of the H11 locus; the phiC31 second recombination site; a reporter gene, a selection marker, or both; Bxb1 second recombination site; a second sequence homologous to a second region of the H11 locus. In certain cases, the landing pad generating construct may include a landing pad cassette comprising from 5' to 3' direction: a first sequence homologous to a first region of the H11 locus; Bxb1 second recombination site; a reporter gene, a selection marker, or both; the phiC31 second recombination site; a second sequence homologous to a second region of the H11 locus. In certain cases, the first sequence homologous to a first region of the H11 locus may be referred to as left homology arm and the second sequence homologous to a second region of the H11 locus may be referred to as the right homology arm.

In certain cases, a first sequence homologous to a first region of the H11 locus and a second sequence homologous to a second region of the H11 locus may be referred to as first and second homology arms. The homology arms may be of similar size or of different size. The first and second homology arms may range in size from 10 nucleotides to 10 kb. In certain cases, the homology arms may be 10 nucleotides or more, 50 nucleotides or more, 100 nucleotides or more, 250 nucleotides or more, 400 nucleotides or more, 500 nucleotides or more, 1000 nucleotides (1 kb) or more, 5000 nucleotides (5 kb) or more, 10000 nucleotides (10 kb) or more etc. The first and second homology arms may have at least 50% sequence identity to a region of the human H11 locus. In certain embodiments, 60%, 70%, 80%, 90%, 95%, 98%, 99%, or 99.9%, or more sequence identity is present.

In some instances, the homology arms may be substantially equal in length to one another, e.g. one may be 30% shorter or less than the other homology arm, 20% shorter or less than the other homology arm, 10% shorter or less than the other homology arm, 5% shorter or less than the other homology arm, 2% shorter or less than the other homology arm, or only a few nucleotides less than the other homology arm. In other instances, the homology arms may be substantially different in length from one another, e.g. one may be 40% shorter or more, 50% shorter or more, sometimes 60% shorter or more, 70% shorter or more, 80% shorter or more, 90% shorter or more, or 95% shorter or more than the other homology arm.

In some instances, the genomic sequences at the human H11 locus to which the flanking homologous sequences have homology are sequences that are used by nucleases or site-specific recombinases, e.g., integrases, resolvases, and the like, to promote site-specific recombination, e.g. as known in the art.

In general, the first sequence and the second sequence at the human H11 target locus to which the first and second homology arms bind may be separated by 0 nucleotides to 10 kb or more, e.g., 0 nucleotides, 5 nucleotides, 10 nucleotides, 20 nucleotides, 50 nucleotides, 80 nucleotides, 100 nucleotides, 500 nucleotides, 1 kb, 2 kb, 3 kb, 4 kb, 5 kb, 10 kb, 20 kb, or more.

Figure 1B:
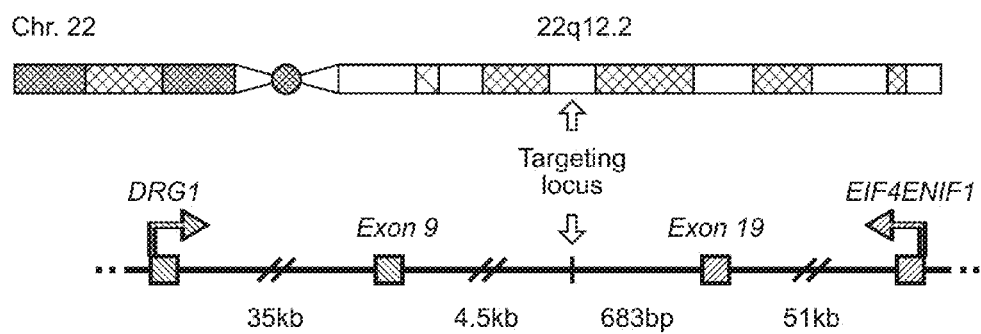

In general, any region in the H11 locus may be used as the target locus. For example, the target locus may be any location in the H11 locus from the 3' of the 3' UTR region of the DRG1 gene to 3' of the 3' UTR region of human EIF4ENIF1 gene. In certain cases, the target locus in the H11 locus may be located 100 bp to 5100 bp downstream of 3' end of the human DRG1 gene, e.g., 2000-5100 bp, 3000-4500 bp, e.g., 100 bp, 300 bp, 500 bp, 1000 bp, 3000 bp, 4000 bp, 4500 bp, 5000 bp downstream of 3' end of the human DRG1 gene. In certain cases, the target locus in the H11 locus may be located 100 bp, 300 bp, 500 bp, 600 bp, 650 bp, 700 bp, 1000 bp, 3000 bp, 4000 bp, 4500 bp, 5000 bp downstream of 3' end of the human EIF4ENIF1 gene. In certain cases, the target locus in the H11 locus may be located 100 bp to 5000 bp downstream of 3' end of the human EIF4ENIF1 gene, e.g., 100 bp-1000 bp, 200 bp-800 bp, 300 bp-700 bp, or 400 bp-700 bp. In certain cases, the target locus for insertion of the phiC31attR and Bxb1 attL sites may be as depicted in FIG. 1B, i.e., 4500-bp downstream of 3' end of DRG1 and 683-bp downstream of 3' end of EIF4ENIF1. In certain embodiments, the first sequence at the H11 locus to which left homology arm is homologous to is a sequence present closer to the centromere and the second sequence at the H11 locus to which right homology arm is homologous to is a sequence present closer to the telomere.

As noted above, the method of inserting a polynucleotide sequence into a genome of a human cell may include an initial step of introducing into the human cell, a circular nucleic acid comprising the phiC31 second recombination site and the Bxb1 second recombination site flanked by a first sequence homologous to a first region of the H11 locus and a second sequence homologous to a second region of the H11 locus. In certain cases, the introducing and maintaining the human cell under conditions that facilitate recombination between the first sequence and the first region and between the second sequence and the second region may result in generation of a recipient cell that includes insertion of the phiC31 second recombination site and the Bxb1 second recombination site at the H11 locus.

In certain cases, the method of inserting a polynucleotide sequence into a genome of a human cell may include introducing into the recipient cell a circular nucleic acid comprising the polynucleotide sequence flanked by a phiC31 first recombination site and a Bxb1 first recombination site; a phiC31 integrase; and a Bxb1 integrase, wherein the recipient cell comprises a phiC31 second recombination site and a Bxb1 second recombination site at H11 locus in chromosome 22; maintaining the recipient cell under conditions that facilitate recombination between phiC31 attB and phiC31 attP sites and between the Bxb1 attB and Bxb1 attP sites, wherein the introducing and maintaining results in insertion of the polynucleotide sequence into the genome of the recipient cell at the H11 locus.

In certain cases, the circular nucleic acid comprising the polynucleotide sequence flanked by a phiC31 first recombination site and a Bxb1 first recombination site may be referred to as a donor construct. The donor construct may include a donor cassette that includes from a 5' to 3' direction: phiC31 first recombination site; a polynucleotide sequence of interest; and a Bxb1 first recombination site. The donor construct may additionally include vector sequence outside the donor cassette that is not inserted into the genome of the human cell. In another embodiment, the donor construct may include a donor cassette that includes from a 5' to 3' direction: a Bxb1 first recombination site; a polynucleotide sequence of interest; and phiC31 first recombination site. The donor cassette for inserting a polynucleotide sequence of interest into a human cell may be selected based on the arrangement of the phiC31 second recombination site and a Bxb1 second recombination site at H11 locus of the recipient cell. For example, when the recipient cell includes phiC31 second recombination site and a Bxb1 second recombination site at H11 locus, where the phiC31 second recombination site is located towards the centromere and the Bxb1 second recombination site is located towards the telomere of chromosome 22, the donor cassette includes from the 5' to 3' direction: phiC31 first recombination site; a polynucleotide sequence of interest; and a Bxb1 first recombination site. Such an arrangement provides for insertion of the donor cassette into the genome but not of the vector sequence in the donor construct. When the recipient cell includes phiC31 second recombination site and a Bxb1 second recombination site at H11 locus, where the Bxb1 second recombination site is located towards the centromere and the phiC31 second recombination site is located towards the telomere of chromosome 22, the donor cassette includes from the 5' to 3' direction: a Bxb1 first recombination site; a polynucleotide sequence of interest; and a phiC31 first recombination site. The polynucleotide sequence of interest may be in either orientation. The donor cassette may include a promoter sequence operably linked to the polynucleotide sequence of interest.

To induce DNA integration in vitro, the maintaining under conditions that facilitate recombination may be carried out for 16-48 hours, after which time the media may be replaced with fresh media and the cells may be cultured further.

Contacting the cells with the circular nucleic acid may occur in any culture media and under any culture conditions that promote the survival of the cells. For example, cells may be suspended in any appropriate nutrient medium, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. Conditions that promote the survival of cells are typically permissive of nonhomologous end joining and homologous recombination.

Nucleic Acid Compositions

As noted above, a first circular nucleic acid is provided. The first circular nucleic acid includes the phiC31 second recombination site and the Bxb1 second recombination site flanked by a first sequence homologous to a first region of the H11 locus and a second sequence homologous to a second region of the H11 locus, as described above. In addition, the first circular nucleic acid may include a reporter gene and/or a selection marker.

In certain cases, the reporter gene may be an "imaging marker". An imaging marker may a non-cytotoxic agent that can be used to locate and, optionally, visualize cells, e.g. cells that have been targeted by nucleic acid compositions of the subject application. An imaging marker may require the addition of a substrate for detection, e.g., horseradish peroxidase (HRP), β-galactosidase, luciferase, and the like. Alternatively, an imaging marker may provide a detectable signal that does not require the addition of a substrate for detection, e.g. a fluorophore or chromophore dye, e.g. Alexa Fluor 488® or Alexa Fluor 647®, or a protein that comprises a fluorophore or chromophore, e.g. a fluorescent protein. As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein and variants thereof.

By a "selection marker" or "selectable marker" it is meant an agent that can be used to select cells, e.g., cells that have been targeted by nucleic acid compositions of the subject application. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Any convenient selectable marker may be employed, for example, a drug selectable marker, e.g. a marker that prevents cell death in the presence of drug, a marker that promotes cell death in the presence of drug, an imaging marker, etc.; an imaging marker that may be selected for using imaging technology, e.g. fluorescence activated cell sorting; a polypeptide or peptide that may be selected for using affinity separation techniques, e.g. fluorescence activated cell sorting, magnetic separation, affinity chromatography, "panning" with an affinity reagent attached to a solid matrix, etc.; and the like.

Also provided herein is a second circular nucleic acid that includes a multiple cloning site flanked by a phiC31 first recombination site and a Bxb1 first recombination site as described above. The multiple cloning site may include sequences recognized by multiple restriction endonucleases. In certain embodiments, the multiple cloning site may include promoter(s) that would be operably linked to a polynucleotide(s) of interest cloned into the multiple cloning site.

Genetically Modified Cells

Also provided herein are genetically modified human cells. In certain cases, the genetically modified human cell may be a recipient cell line that includes at the H11 locus, a phiC31 second recombination site and the Bxb1 second recombination site.

In certain cases, the genetically modified human cell may be a human cell that includes a polynucleotide sequence of interest at the H11 locus flanked by a recombined recognition sequence of phiC31 integrase and a recombined recognition sequence of Bxb1 integrase.

In certain cases, the recipient cell that includes insertion of the phiC31 second recombination site and the Bxb1 second recombination site at the H11 locus may be isolated or enriched prior to the step of introducing into the human cell: a circular nucleic acid comprising the polynucleotide sequence flanked by a phiC31 first recombination site and a Bxb1 first recombination site; a phiC31 integrase; and a Bxb1 integrase.

In certain cases, the human cell that is genetically modified to include a polynucleotide sequence of interest may be isolated or enriched.

Separation of genetically modified cells typically relies upon the expression of a selectable marker that is co-integrated into the target locus. By a "selectable marker" it is meant an agent that can be used to select cells, e.g. cells that have been targeted by compositions of the subject application. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Separation may be by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells.

Cell compositions that are highly enriched for cells comprising the polynucleotide sequence of interest are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been genetically modified in this way may be transplanted to a human subject for purposes such as gene therapy, e.g. to treat a disease, or as an antiviral, antipathogenic, or anticancer therapeutic. The subject may be a neonate, a juvenile, or an adult.

The genetically modified cells of the present invention may be formulated into cell compositions that are pharmaceutical compositions that include a pharmaceutically acceptable carrier. Examples of pharmaceutically acceptable carriers include saline, buffers, diluents, fillers, salts, stabilizers, solubilizers, cell culture medium, and other materials which are well known in the art. In some embodiments, the formulations are free of detectable DMSO (dimethyl sulfoxide).

Any human cell's genome may be modified by the nucleic acid compositions and methods described herein. For example, the cell may be a meiotic cell, a mitotic cell, or a post-mitotic cell. Mitotic and post-mitotic cells of interest in these embodiments include pluripotent stem cells, e.g. ES cells, iPS cells, and embryonic germ cells; and somatic cells, e.g. fibroblasts, hematopoietic cells, neurons, muscle cells, bone cells, vascular endothelial cells, gut cells, and the like, and their lineage-restricted progenitors and precursors.

Cells may be modified in vitro or in vivo. If modified in vitro, cells may be from established cell lines or they may be primary cells, where "primary cells", "primary cell lines", and "primary cultures" are used interchangeably herein to refer to cells and cells cultures that have been derived from a subject, such as, a human subject and either modified without significant additional culturing, i.e. modified "ex vivo", e.g. for return to the subject, or allowed to grow in vitro for a limited number of passages, i.e. splittings, of the culture. For example, primary cultures are cultures that may have been passaged 0 times, 1 time, 2 times, 4 times, 5 times, 10 times, or 15 times. Typically, the primary cell lines of the present disclosure are maintained for fewer than 10 passages in vitro.

If the cells are primary cells, they may be harvested from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, nervous system, etc., are most conveniently harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

PhiC31 and Bxb1 Integrases

PhiC31 and Bxb1 integrases used in the methods described herein include variant phiC31 and Bxb1 integrases that retain their activity that mediates site-specific recombination between specific DNA sequences recognized by the intergrases. Integrases are also referred to as recombinases.

"Variant recombinases" include "mutant recombinases" are used interchangeably herein to refer to recombinase enzymes in which the native, wild-type recombinase gene found in the organism of origin has been mutated in one or more positions relative to a parent recombinase (e.g., in one or more nucleotides, which may result in alterations of one or more amino acids in the altered recombinase relative to a parent recombinase). "Parent recombinase" is used to refer to the nucleotide and/or amino acid sequence of the recombinase from which the altered recombinase is generated. The parent recombinase can be a naturally occurring enzyme (i.e., a native or wild-type enzyme) or a non-naturally occurring enzyme (e.g., a genetically engineered enzyme). The mutations present in an altered recombinase may comprise base substitutions, deletions, additions, and/or other rearrangements in the DNA sequence encoding the recombinase, and/or any combination of such mutations, either singly or in groups.

A "recognition site" is a DNA sequence that serves a substrate for a wild-type or variant recombinase so as to provide for unidirectional site-specific recombination. In general, the recombinases used in the invention involve two recognition sites, one that is positioned in the integration site (the site into which a nucleic acid is to be integrated) and another adjacent a nucleic acid of interest to be introduced into the integration site. For example, the recognition sites for phage integrases phiC31 and Bxb1 are generically referred to as attB and attP. Recognition sites can be native or altered relative to a native sequence. Use of the term "recognize" in the context of a recombinase "recognizes" a recognition sequence, is meant to refer to the ability of the recombinase to interact with the recognition site and facilitate site-specific recombination.

In certain cases, the phiC31 attB and attP site sequences and the phiC31 integrase may be as provided in U.S. Pat. No. 8,304,233 or U.S. Pat. No. 8,420,395, the entire disclosures of which are herein incorporated by reference.

In certain cases, the Bxb1 attB and attP site sequences and the Bxb1 integrase may be as provided in US 20110136237 and US 20080020465, the entire disclosures of which are herein incorporated by reference.

Utility

The nucleic acid compositions, cell compositions, and methods disclosed herein find use in any in vitro or in vivo application in which it is desirable to express one or more polynucleotide sequences/genes of interest in a human cell.

For example, the subject methods and compositions may be used to treat a disorder, a disease, or medical condition in a subject. Towards this end, the one or more genes of interest to be integrated into a cellular genome may include a gene that encodes for a therapeutic agent. By a "therapeutic agent" it is meant an agent, e.g. siRNA, shRNA, miRNA, CRISPRi agents, peptide, polypeptide, suicide gene, etc., that has a therapeutic effect upon a cell or an individual, for example, that promotes a biological process to treat a medical condition, e.g. a disease or disorder. The terms "individual," "subject," "host," and "patient," are used interchangeably herein and refer to any human subject for whom diagnosis, treatment, or therapy is desired. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

Examples of therapeutic agents that may be integrated into a cellular genome using the subject methods and compositions include agents, i.e., siRNAs, shRNAs, miRNAs, CRISPRi agents, peptides, or polypeptides, which alter cellular activity. Other examples of therapeutic agents that may be integrated using the subject methods and compositions include suicide genes, i.e., genes that promote the death of cells in which the gene is expressed. Non-limiting examples of suicide genes include genes that encode a peptide or polypeptide that is cytotoxic either alone or in the presence of a cofactor, e.g., a toxin such as abrin, ricin A, *pseudomonas* exotoxin, cholera toxin, diphtheria toxin, Herpes Simplex Thymidine Kinase (HSV-TK); genes that promote apoptosis in cells, e.g. Fas, caspases (e.g. inducible Caspase9) etc.; and genes that target a cell for ADCC or CDC-dependent death, e.g. CD20.

In some instances, the therapeutic agent alters the activity of the cell in which the agent is expressed. In other words, the agent has a cell-intrinsic effect. For example, the agent may be an intracellular protein, transmembrane protein or secreted protein that, when expressed in a cell, will substitute for, or "complement", a mutant protein in the cell. In other instances, the therapeutic agent alters the activity of cells other than cells in which the agent is expressed. In other words, the agent has a cell-extrinsic effect. For example, the integrated gene of interest may encode a cytokine, chemokine, growth factor, hormone, antibody, or cell surface receptor that modulates the activity of other cells.

The subject methods and compositions may be applied to any disease, disorder, or natural cellular process that would benefit from modulating cell activity by integrating a gene of interest. For example, the subject agents and methods find use in treating genetic disorders. Any genetic disorder that results from a single gene defect may be treated by the subject compositions and methods, including, for example, neurodegenerative diseases, e.g., Parkinson's' disease, hemophilia, adenosine deaminase deficiency, sickle cell disease, X-Linked Severe Combined Immunodeficiency (SCID-X1), thalassemia, cystic fibrosis, alpha-1 anti-trypsin deficiency, diamond-blackfan anemia, Gaucher's disease, growth hormone deficiency, and the like. As another for example, the subject methods may be used to in medical conditions and diseases in which it is desirable to ectopically express a therapeutic agent, e.g. siRNA, shRNA, miRNA, CRISPRi agent, peptide, polypeptide, suicide gene, etc., to promote tissue repair, tissue regeneration, or protect against further tissue insult, e.g. to promote wound healing; promote the survival of the cell and/or neighboring cells, e.g. in degenerative disease, e.g. neurodegenerative disease, kidney disease, liver disease, etc.; prevent or treat infection, etc.

As one non-limiting example, the subject methods may be used to integrate a gene encoding a neuroprotective factor, e.g. a neurotrophin (e.g. NGF, BDNF, NT-3, NT-4, CNTF), Kifap3, Bcl-xl, Crmpl, Chkβ, CALM2, Caly, NPG11, NPT1, Eef1a1, Dhps, Cd151, Morf412, CTGF, LDH-A, Atl1, NPT2, Ehd3, Cox5b, Tubala, γ-actin, Rpsa, NPG3, NPG4, NPG5, NPG6, NPG7, NPG8, NPG9, NPG10, etc., into the genome of neurons, astrocytes, oligodendrocytes, or Schwann cells at a locus that is active in those particular cell types (for example, for neurons, the neurofilament (NF), neuro-specific enolase (NSE), NeuN, or Map2 locus; for astrocytes, the GFAP or S100B locus; for oligodendrocytes and Schwann cells, the GALC or MBP locus). Such methods may be used to treat nervous system conditions and to protect the CNS against nervous system conditions, e.g. neurodegenerative diseases, including, for example, e.g. Parkinson's Disease, Alzheimer's Disease, Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression), childhood disorders (e.g. attention deficit disorder, autistic disorders), cognitive disorders (e.g. delirium, dementia), schizophrenia, substance related disorders (e.g. addiction), eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, traumatic brain injury, and spinal cord injury.

In certain embodiments, the subject methods find use in treating muscular dystrophy, such as, Duchenne muscular dystrophy, limb girdle muscular dystrophy 2B, and limb girdle muscular dystrophy 2D. When used to treat Duchenne muscular dystrophy in a subject, the polynucleotide sequence inserted into the genome of the human cell may include a polynucleotide encoding dystrophin, such as, full length dystrophin or functional fragments or a functional variant thereof. In certain cases, a subject having limb girdle muscular dystrophy 2B may be treated using the subject methods, where the polynucleotide sequence inserted into the genome of the human cell may encode for dysferlin or a functional fragment or a functional variant thereof. In certain cases, a subject having limb girdle muscular dystrophy 2D may be treated using the subject methods, where the polynucleotide sequence inserted into the genome of the human cell may encode alpha-sarcoglycan or a functional fragment or a functional variant thereof. In certain cases, the human cell may be an iPS cell derived from a cell of the subject being treated.

Other examples of how the subject methods may be used to treat medical conditions are disclosed elsewhere herein, or would be readily apparent to the ordinarily skilled artisan.

As discussed above, any gene of interest may be integrated into a target locus, for example, any gene encoding an siRNA, shRNA, miRNA, CRISPRi element, peptide, or polypeptide may be integrated. Additionally, as discussed above, more than one gene of interest may be integrated, for example, two or more genes of interest may be integrated, three or more genes may be integrated, four or more genes may be integrated, e.g. five or more genes may be integrated. Thus, for example, in an embodiments where the genetically modified cell is a ES or PS or iPS cell, the one of more polynucleotide sequences/genes of interest may be transcription factors that promote the differentiation of the ES or PS or iPS cell into a particular cell lineage. For example, the subject methods may be used to convert iPS generated from a somatic cell isolated from a subject in need of a particular cell type into the particular cell type. Since the cells to be transplanted into the subject are derived from the subject's cells, any immune response to the transplanted cells may be reduced or avoided.

Integrating one or more genes of interest into genomic DNA such that it is expressed in cell finds use in many fields, including, for example, gene therapy, and research. For example, such modifications are therapeutically useful, e.g. to treat a genetic disorder by complementing a genetic mutation in a subject with a wild-type copy of the gene; to promote naturally occurring processes, by promoting/augmenting cellular activities (e.g. promoting wound healing for the treatment of chronic wounds or prevention of acute wound or flap failure, by augmenting cellular activities associated with wound healing); to modulate cellular response (e.g. to treat diabetes mellitus, by providing insulin); to express antiviral, antipathogenic, or anticancer therapeutics in subjects, e.g. in specific cell populations or under specific conditions, etc. Other uses for such genetic modifications include in the induction of induced pluripotent stem cells (iPSCs), e.g. to produce iPSCs from an individual for diagnostic, therapeutic, or research purposes; in the production of genetically modified cells, for example in manufacturing for the large scale production of proteins by cells for therapeutic, diagnostic, or research purposes.

The genetically modified cells of the present disclosure may be provided to the human subject alone or with a suitable substrate or matrix, e.g., to support their growth and/or organization in the tissue to which they are being transplanted. Usually, at least $1\times10^3$ cells may be administered, for example $5\times10^3$ cells, $1\times10^4$ cells, $5\times10^4$ cells, $1\times10^5$ cells, $1\times10^6$ cells or more. The cells may be introduced to the subject via any of the following routes: parenteral, subcutaneous, intravenous, intracranial, intraspinal, intraocular, intramuscular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. US Application No. 20070254842, incorporated here by reference); or by implanting a device upon which the cells have been reversably affixed (see e.g. US Application Nos. 20080081064 and 20090196903, incorporated herein by reference).

The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

Kits

Also provided are kits for practicing one or more of the above-described methods. The subject kits may have a combination of nucleic acid compositions as described herein, or recipient cells as described herein, or a both. Reagents of interest may include polynucleotide compositions, e.g. a vector comprising H11 locus specific left homology arm, phiC31 second recombination site, a reporter gene or a selection marker or both, Bxb1 second recombination site, H11 locus specific right homology arm; a vector comprising phiC31 first recombination site, a cloning site that includes restriction enzyme sites for cloning of a polynucleotide sequence of interest; a nucleic acid encoding phiC31, a nucleic acid encoding Bxb1. Other non-limiting examples of reagents include targeted nuclease compositions, e.g. a target nuclease or pair of targeted nucleases specific for the target site in the H11 locus; reagents for selecting cells genetically modified with the integrated gene of interest; and positive and negative control vectors or cells comprising integrated positive and/or negative control sequences for use in assessing the efficacy donor polynucleotide compositions in cells, etc.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Materials and Methods

Plasmid Construction

PCR reactions for plasmid construction were performed with either Phusion DNA polymerase (New England Biolabs, Ipswich, Mass.) or KAPA HiFi HotStart ReadyMix (2×) (KAPA Biosystems, Woburn, Mass.). All DNA fragments amplified by PCR were completely sequenced after cloning. Primers used to generate the homology arms are listed in Table 1.

and the control plasmid lacking transcription factors were generated based on the p2attPC-LFO plasmid. Transcription factor cDNA sequences were purchased from DNASU, the DNA repository at Arizona State University. Plasmid sequences will be made available upon request.

For TALEN targeting plasmid construction, TALEN (repeat variable diresidue) RVDs were designed by the TAL Effector Nucleotide Targeter 2.0 (Cermak, T. et al., *Nucleic Acids Res.*, 2011, 39, e82; Doyle, E. L., *Nucleic Acids Res.*, 2012, 40, W117-W122) (spacer 15-24, RVDs=15-20). TALEN-encoding plasmids were assembled using the Golden Gate TALEN assembly library (Addgene) according to the provided instructions with modified FokI, which was cloned into a mammalian expression vector. The efficiency of induction of double-strand breaks by TALE pairs was determined by using the SURVEYOR® Mutation Detection Kit (Transgenomic Inc., Omaha, Nebr.).

Cell Culture and Differentiation

Human pluripotent stem cells, including H9 ESC, PI-1761 and PI-1754 iPSC, and subclones derived from

| Name | Sequence (5' to 3') | Purpose |
|---|---|---|
| 302 | ATCGGCGGCCGCGGCGCGCCCCTTTTTCCTTGAGCTTTAAAGACCCCAACAGGTCAG | 5' HR homology arm F |
| 303 | ATCGGTCGACGCTCTTGGGAAGAAGTCAAACATTATTTCAG | 5' HR homology arm R |
| 301 | ATCGGTCGACGGCGCGCCATTTAAATGTTTAAACCCATAGTTGATTTCTCCTAAATCAAGATAGAGTCC | 3' HR homology arm F |
| 305 | ATCGGCGGCCGCCCGCGGTTAATTAACCAAATGATTAATCCTGATGGCTGAGGAGAC | 3' HR homology arm R |
| H11 5-1 | AATTATTTAAATGACTCAGAACTGTACTGTAT | 5' TALEN homology arm F |
| H115-2 | AATTAGATCTCCTTTTTCCTTGAGCTTTAA | 5' TALEN homology arm R |
| H11 3-1 | AATTGGCGCGCCAGTATGTTCCTTTAAGGAAG | 3' TALEN homology arm F |
| H11 3-2 | AATTGGCGCGCCAGTATGTTCCTTTAAGGAAG | 3' TALEN homology arm R |
| T9 | ACCCAGTCCGCCCTGAGCAA | HR master gPCR F |
| HN3R1 | TGGGCAGAAGGGAGGGTATGGACATGTAAG | HR master gPCR R |
| H4005F4 | AGTTCCAGGCTTATAGTCATTATTCCCTAA | TALEN master gPCR F |
| N-5R3 | GTCTCATGAGCGGATACATATTTGAATGTA | TALEN master gPCR R |
| Gprobe F | GACGGCGACGTAAACGGCCA | Southern G probe F |
| GprobeR | TTGCTCAGGGCGGACTGGGT | Southern G probe R |
| H400-5F1 | CCAACCACCTTGACCTTTACCTCATTATCT | Second allel F/HR DICE R |
| N2 | CTGCAGTCCAGCCTGGCGAC | Second allele R |
| CE-bxb1-F2 | ACGGCGGTCTCCGTCGTCAG | HR DICE F |
| H400-5F2 | AAGCTGAGGAATCACATGGAGTGAATAGCA | TALEN DICE F |
| CE-attB-R2 | GGGTGGGGCAGGACAGCAAG | TALEN DICE R |

Figure 2A:
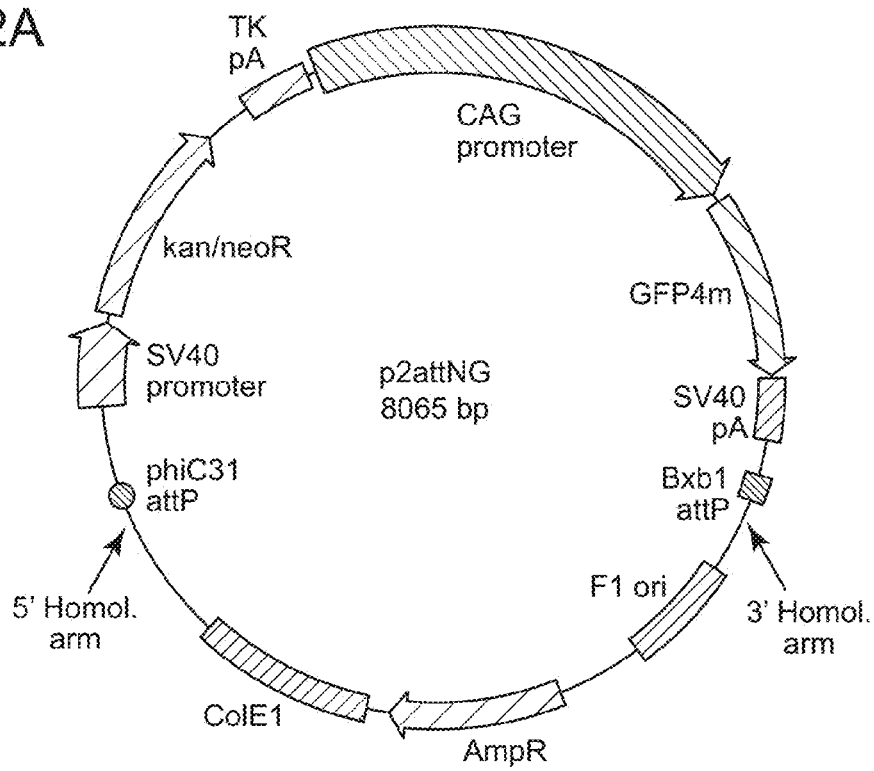
FIGS. 2A-2B depict plasmid maps of the landing pad construct (FIG. 2A) and the donor cassette construct (FIG. 2B).

For the landing pad plasmid p2attNG, the structure of the Neo and GFP exchange cassette is provided in FIG. 2A. The homology arms for homologous recombination at the human H11 locus in the landing pad plasmid were 5 kb and 3 kb in length, while homology arms of 400 bp on each side were used for transcription activator-like effector nuclease (TALEN)-assisted recombination. For the donor plasmid, the structure of plasmid p2attPC-LFO is provided in FIG. 2B. The constructs with two of the three transcription factors these cells, were cultured on irradiation-inactivated mouse embryo fibroblasts (MEF) in human stem cell culture medium consisting of Dulbecco's modified eagle medium/F12 (DMEM/F12), 20% knockout serum replacement (KSR), 0.1 mM non-essential amino acids (NEAA), 2 mM glutamax, 0.1 mM β-mercaptoethanol (2-ME) (all from Invitrogen, Carlsbad, Calif.), and 10 ng/mL bFGF (R&D Systems, Minneapolis, Minn.). Culture medium was changed daily. H9 and PI-1761 cells were passaged every 5-7 days using 1 mg/mL collagenase IV (Invitrogen), while PI-1754 Parkinson's disease patient iPSC were manually passaged every 7-10 days.

For embryoid body (EB)-mediated differentiation, cells were incubated with 1 mg/mL dispase (Invitrogen) for 15 minutes, washed, and then colonies were harvested and transferred from 6-well plates to ultra low attachment surface 6-well plates (Corning, Tewksbury, Mass.) in differentiation medium containing DMEM/F12, 15% fetal bovine serum (FBS, Invitrogen), 0.1 mM NEAA, 2 mM glutamax, and 0.1 mM 2-ME. Medium was changed every 2-3 days. After 8 days in suspension culture, EBs were collected, reseeded onto 24-well plates pre-coated with 0.1% gelatin (Sigma Aldrich, St. Louis, Mo.), and cultured for another 8 days in the same medium.

Nucleofection and Stable Line Generation

Nucleofection was performed using the P3 Primary Cell 4D-Nucleofector® X Kit L (Lonza, Walkersville, Md.) according to the manufacturer's instructions. Briefly, cells were dissociated with Accutase (Millipore, Billerica, Mass.) into single cells, depleted of MEF feeders, and counted. Then $0.8-1.6 \times 10^6$ cells were nucleofected in one cuvette and quickly reseeded onto multi-antibiotic resistant DR4 MEF cells (Applied StemCell, Menlo Park, Calif.) freshly prepared one day earlier. The Rho kinase inhibitor Y27632 (Tocris Bioscience, Bristol, UK) was used 24 h before and after nucleofection to promote cell survival.

For generation of recipient ESC and iPSC lines, 5 µg landing pad plasmid were used for spontaneous homologous recombination, and 8 µg landing pad plasmid and 1 µg TALEN-encoding plasmids were used for TALEN-mediated recombination. For DICE, 4 µg were used for each of phiC31 integrase (pCS-kl; (Farruggio, A. P., et al., *Biotechnol., J.,* 2012, 7, 1332-1336), Bxb1 integrase (pCMV-Bx; (Keravala, A., et al., Mol. Genet. Genomics, 2006, 276, 135-146), and attB donor plasmids. Cells were selected with either 50 µg/ml G418 (Invitrogen) for homologous recombination or 500 ng/ml puromycin (Invitrogen) for DICE, starting 2-4 days after nucleofection, and exposing cells to puromycin for only 2-3 days. Surviving clones that were mCherry-positive and GFP-negative were picked 2 weeks after drug selection and expanded for further experiments.

Genomic PCR

Genomic DNA was extracted using ZR Genomic DNA II kit (Zymo Research Corp., Irvine, Calif.) or QuickExtract™ DNA Extraction Solution (Epicentre Biotechnolgies, Madison, Wis.) according to the manufacturer's instructions. Genomic PCR was performed with GoTaq® Green Master Mix (Promega Biosystems, Sunnyvale, Calif.). Primers used are listed in Table 1.

Southern Blotting

Genomic DNA was purified from cells by standard phenol/chloroform extraction and digested with ScaI-HF (New England Biolabs) for 6-8 hours, supplemented with 1 mM spermidine (Sigma), 100 µg/ml bovine serum albumin (BSA, Sigma), and 50 µg/ml RNAse A (Millipore). 10 µg digested DNA from each clone were separated on 0.8% agarose gels and transferred to hybond-N+ nylon membrane (GE Healthcare, Piscataway, N.J.). The GFP probe targeted to the GFP transgene was generated by PCR, and the primer sequences are listed in Table 1. The labeling of probe and hybridization with the membranes were performed according to the manufacturer's instructions (Amersham Rediprime II labeling system, GE Healthcare).

Immunocytochemistry

Cells were fixed in 4% (wt/vol.) paraformaldehyde (Electron Microscopy Sciences, Hatfield, Pa.) for 20 minutes, rinsed with PBS, permeabilized, and blocked by 3% normal donkey serum (Jackson ImmunoResearch Laboratories, Bar Harbor, Me.) in PBST (PBS+0.2% TritonX-100; Sigma) for 60 minutes at room temperature. Cells were incubated with primary antibodies in PBST at 4° C. overnight and then washed with PBS three times. Then cells were incubated with secondary antibodies diluted in PBS containing 0.1% BSA (Jackson ImmunoResearch Laboratories) for 1 hour at room temperature. Finally, the cells were counter-stained for nuclei with 1 µg/ml DAPI (Roche, Nutley, N.J.).

Primary antibodies used in this study include rabbit anti-OCT3/4, rabbit anti-SOX2, rabbit anti-NANOG, mouse anti-SSEA4 (all from Cell Signaling Technology, Beverly, Mass.), mouse anti-TRA-1-60 (Millipore), mouse anti-TRA-1-81 (Millipore), mouse anti-AFP (Cell Signaling Technology), mouse anti-alpha-SMA (Abcam, Burlingame, Calif.), mouse anti-βIII-Tubulin (Covance, Princeton, N.J.), goat anti-FOXA2 (R&D Systems), rabbit anti-OTX2 (Millipore), and rabbit anti-LMX1a (Millipore). Secondary antibodies were Alexa Fluor 488/594-conjugated donkey anti-mouse/rabbit/goat (Jackson ImmunoResearch Laboratories).

Karyotyping

G-banded karyotyping was performed by WiCell Cytogenetic Services, Madison, Wis.

Example 1: H11 Locus and DICE

We previously described a transcriptionally and recombinationally active, ubiquitously expressed murine locus called Hipp11 (Hippenmeyer, et al. (2010) *Neuron,* 68, 695-709; Tasic, et al. (2011) *Proc Natl Acad Sci USA,* 108, 7902-7907; Tasic, et al. (2012) *PLoS One,* 7, e33332). Hipp11 is located in an intergenic region on chromosome 11, flanked by the two genes Drg1 and Eif4enif1 (Hippenmeyer, et al., 2010, supra). The criteria for identification of the Hipp11 locus included absence of disruption of regulatory elements or genes, as judged by sequence annotation, an intergenic region in a gene dense area, a location at the convergence between two genes transcribed in opposite directions, and apparently ubiquitous transcriptional activity, as reflected by broad spatial and temporal expressed sequence tag (EST) expression patterns, indicating ubiquitous transcriptional activity. This latter feature is especially important in stem cells, where during differentiation, chromatin remodeling typically leads to silencing of some loci and potential activation of others. Within the region, a precise locus was chosen that was devoid of repetitive elements and conserved sequences and to which primers for amplification of homology arms could easily be designed. In vivo experiments verified that integration of targeting cassettes at Hipp11 did not interfere with viability or fertility of mice and that biallelic expression of targeting cassettes was possible. Studies in mice confirmed that genes inserted at Hipp11 displayed robust, ubiquitous expression that appeared to be superior to the expression levels of other commonly used ubiquitously active loci, including ROSA26 (Hippenmeyer, et al., 2010, supra; Tasic, et al., 2011, supra; Tasic, et al., 2012, supra).

To identify the orthologous locus in the human genome, we first located DRG1 and EIF4ENIF1 in human chromosomes and located the human equivalent locus, called H11, by its distance from these two genes. Human DRG1 and EIF4ENIF1 are located on chromosome 22q12.2, the distance between the two genes is very similar between mouse and human, and the intron/exon organization of DRG1 and EIF4ENIF1 is highly conserved between the two species.

We screened the region about 700 bp 3' to the 3' UTR of human EIF4ENIF1 and chose a locus where primers could readily be designed for amplification of homology arms, 4500-bp downstream of DRG1 and 683-bp downstream of EIF4ENIF1 (FIG. 1B). The level of DNA sequence identity between the mouse Hipp11 and human H11 regions was approximately 45%, similar to the average sequence identity between mouse and human of 40%, reflecting the absence of highly conserved sequences in the region and consistent with a safe region for insertion of transgenes. Because of the parallels with the mouse location, we speculated that the H11 locus would allow strong expression of inserted genes without disrupting endogenous gene function.

We then combined the human H11 locus, spontaneous or TALEN-assisted homologous recombination, and phiC31 and Bxb1 integrases to create an efficient site-specific integration system for ESC and iPSC. The overall strategy is shown in FIG. 1A. The landing pad construct carried neomycin resistance and GFP genes for selection and screening, flanked by attP sites for phiC31 and Bxb1 integrases. This cassette was placed into the human H11 locus by using either spontaneous or TALEN-assisted homologous recombination, to generate recipient ESC and iPSC lines. Neomycin selection was used to identify clones that had integrated the landing pad, while GFP expression provided an indication of the level of gene expression from the locus.

In the second step, we performed dual integrase cassette exchange (DICE) to introduce the genes of interest into the H11 locus in the recipient cell lines. PhiC31 integrase and Bxb1 integrase were combined to generate a high degree of specificity and directionality for the cassette exchange reaction. The donor cassette carried puromycin resistance and mCherry genes for selection and screening, in addition to the gene of interest, for example, neural transcription factor genes. These donor genes were flanked by attB sites for phiC31 and Bxb1, to target site-specific recombination. PhiC31 and Bxb1 integrases recognize and recombine their attP and attB sites with a high degree of specificity using concerted cut- and paste recombination events (Grindley et al. (2006) *Annu. Rev. Biochem.*, 75, 567-605), and all genes internal to the attB sites will be inserted into the genome in a defined orientation and copy number. Therefore, in this system, DICE will ensue when the donor plasmid along with phiC31 and Bxb1 integrase-expressing plasmids are co-transfected into recipient cell lines. Through this two-step strategy, which combines genome editing methods mediated by homologous recombination and by site-specific integrases, we established a highly specific, precise, and convenient system for editing ESC and iPSC genomes.

FIG. 1. DICE strategy and H11 location. (A) Schematic diagram describing a two-step process for robust and easily repeatable placement of any genes into human pluripotent stem cells. First, the attP-flanked Neo-GFP landing pad is introduced into the H11 locus by homologous recombination (HR) to generate a recipient cell genome. The position of the probe (G probe) used to characterize the recipient cell lines by Southern blotting is indicated. Then, the donor gene cassette is recombined into this location by dual integrase cassette exchange (DICE). In this case, the donor cassette carries genes for neural transcription factors (TF), as well as puromycin resistance and mCherry genes for selection and screening. (B) Location of the H11 locus in the human genome. H11 resides in an intergenic region on chromosome 22q12.2, flanked by the DRG1 and EIF4ENIF1 genes. The distances from H11 to the terminal exons of the two flanking genes are indicated.

Figure 3A:
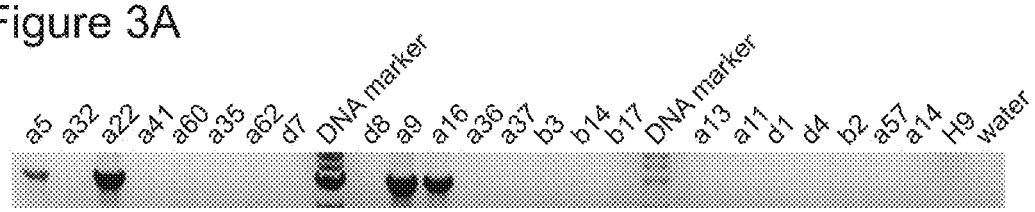
FIGS. 3A-3C pertain to generation of recipient ESC and iPSC lines.

Example 2: Homologous Recombination at the H11 Locus and Generation of Recipient Cell Lines We first utilized spontaneous homologous recombination to insert the landing pad cassette into the H11 locus in H9 ESC. The targeting vector contained an expression cassette carrying the neomycin resistance and GFP genes, flanked by the attP sites for phiC31 and Bxb1 integrases and two homology arms, of 5-kb and 3-kb (FIG. 2A). The targeting vector was linearized by digestion with SwaI and AscI and introduced into H9 cells by an optimized nucleofection protocol. G418 selection was started two days later and continued for 14 days, after which GFP-positive clones were picked and screened by genomic PCR and Southern blotting. Out of 98 clones analyzed, 6 underwent the desired recombination event (FIG. 3A), indicating a targeting frequency of 6.1% in H9 ESC (Table 2).

TABLE 2

Summary of homologous recombination experiments for generation of recipient ESC and iPSC lines. The last column shows the percentage of correctly targeted clones for each condition. HR = homologous recombination

| Cell line | Targeting method | Landing pad | # of clones analyzed | # of correctly targeted clones | Targeting efficiency (%) |
|---|---|---|---|---|---|
| H9 ESC | Spontaneous HR | 5 kb arm-Neo-GFP-3 kb arm | 98 | 6 | 6.1 |
| 1761 iPSC | Spontaneous HR | 5 kb arm-Neo-GFP-3 kb arm | 35 | 2 | 5.7 |
| 1754 iPSC | Spontaneous HR | 5 kb arm-Neo-GFP-3 kb arm | 23 | 0 | 0 |
| H9 ESC | TALEN-assisted HR | 0.4 kb arm-Neo-GFP-0.4 kb arm | 12 | 7 | 58.3 |
| 1761 iPSC | TALEN-assisted HR | 0.4 kb arm-Neo-GFP-0.4 kb arm | 33 | 15 | 45.5 |
| 1754 iPSC | TALEN-assisted HR | 0.4 kb arm-Neo-GFP-0.4 kb arm | 24 | 13 | 54.2 |

We then asked whether iPSC could be genetically modified at the H11 locus by the same method. For these experiments, we used PI-1754 iPSC from a Parkinson's disease (PD) patient (Byers, et al. (2011) *PLoS ONE*, 6, e26159) and PI-1761 iPSC from a normal sibling control. The PI-1754 iPSC line was generated from a PD patient with a triplication of the alpha-synuclein (SNCA) gene, and it exhibits PD-related pathological phenotypes in culture after differentiation into dopaminergic neurons (Byers, et al., 2011, supra). The landing pad vector for the iPSC was the same as that used for H9, except that the homology arm sequences were slightly different, reflecting minor DNA polymorphisms observed between these three human genomes. Similar procedures were performed to carry out homologous recombination in PI-1754 and PI-1761 iPSC. For the normal sibling control PI-1761, two correctly targeted clones were identified out of 35 picked (5.7%; Table 2). However, we failed to get any correctly targeted clones among 23 clones picked for the PD patient-derived PI-1754 iPSC. This result may have been due to the disease-related phenotype of the PI-1754 iPSC, which is reflected in poor growth and propensity for differentiation upon passaging and after nucleofection. This phenotype is in contrast to the robust growth of the wild-type PI-1761 iPSC and H9 ESC lines, even after passaging and nucleofection.

In an attempt to stimulate the frequency of homologous recombination, which appeared critical for PI-1754 iPSC, we applied the recently-described TALEN genome-editing method to generate double-strand breaks in a site-specific manner. Such breaks can be used to target the spontaneous homologous recombination system at an elevated frequency. Transcription activator-like effectors (TALEs) are a newly described class of specific DNA binding proteins from *Xanthomonas* plant pathogens (Boch, et al., 2009, *Science*, 326, 1509-1512). These proteins contain DNA-binding domains of TALE repeats composed of 33-35 amino acids. The TALE repeats have almost identical sequences, except for the "repeat variable di-residue" (RVD), which specifically recognize one target base. Repeats with the appropriate specificity are linked to a nuclease domain to generate a TALE-nuclease (TALEN). TALENs are straightforward to design and construct (Cermak, et al. (2011) *Nucleic Acids Res.*, 39, e82) and induce double-strand breaks in specific DNA sequences. The breaks will be repaired by the cell using either homology-directed repair or the error-prone process of nonhomologous end-joining (NHEJ). TALENs have been shown to be effective for genome editing in human pluripotent stem cells (Hockemeyer, et al. (2011) *Nat. Biotechnol.*, 29, 731-734), although as with other methods of artificially stimulating homologous recombination through provision of targeted double-strand breaks, off-target effects and unwanted mutagenesis can occur.

Figure 3B:
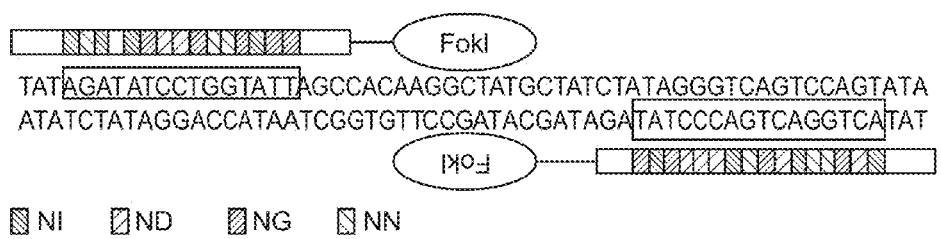

We identified two potential TALEN target sites (Spacer=15-24 bp, RVDs=15-20 bp) for the H11 locus using the TAL Effector Nucleotide Targeter 2.0 (Cermak, et al., 2011, *Nucleic Acids Res.*, 39, e82; Doyle, et al., 2012, *Nucleic Acids Res.*, 40, W117-W122), with one located exactly at the H11 locus, while the other was 60-bp from the locus. TALEN pairs were assembled according to the Golden Gate methodology (Cermak, et al. (2011) *Nucleic Acids Res.*, 39, e82) (FIG. 3B). We then determined the efficiency of these two pairs of TALENs to make double-strand breaks in the K562 cell line by a mutation detection kit. This assay is based on the generation of PCR products that are subsequently hybridized to generate mismatches in heteroduplexed DNA, and cleavage of the mismatches by a nuclease. According to this assay, the second TALEN pair (FIG. 3B) showed a higher efficiency of double-strand breaks of approximately 25% and was therefore chosen for genomic manipulation in ESC and iPSC.

Figure 3C:
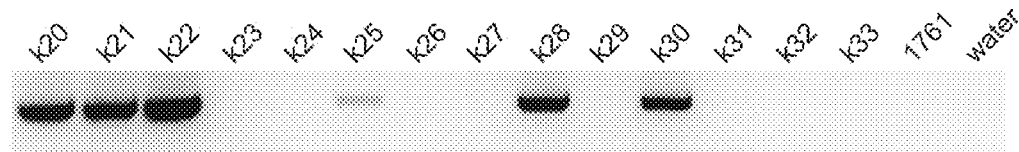

For TALEN-assisted homologous recombination at the H11 locus in ESC and iPSC, we used the same landing pad plasmid that was used for spontaneous recombination. However, shorter homology arms, of only 400-bp of homologous sequences flanking H11, were employed. We introduced the two TALEN expression vectors and the landing pad plasmid into H9 ESC and PI-1761 and PI-1754 iPSC by nucleofection. After similar neomycin drug selection and GFP screening procedures, genomic PCR analysis (FIG. 3C), revealed that 7 out of 12, 15 out of 33, and 13 out of 24 clones underwent the correct the recombination event in H9 ESC, 1761 and 1754 iPSC, respectively, indicating a targeting efficiency of ~40%-50%, even for the PD patient 1754 iPSC (Table 2). These results represented a dramatic increase in recombination frequency of ~8-fold at the H11 locus in human ESC and iPSC mediated by TALEN-assisted homologous recombination. Therefore, the TALEN system was efficient for genomic editing, even in disease iPSC where spontaneous homologous recombination was ineffective.

FIG. 2. Plasmid maps of the landing pad construct (A) and the donor cassette construct (B), where the LFO plasmid bearing three transcription factors (LMX1a-FOXA2-OTX2) is shown as an example. The phiC31 and Bxb1 attP site fragments used in p2attNG were 221 bp and 253 bp in length, respectively. In all donor cassette constructs, the phiC31 and Bxb1 attB site fragments were 285 bp and 300 bp in size, respectively. Homology arms (not shown) were added to p2attNG upstream of the phiC31 attP site and downstream of the Bxb1 attP sequence (arrows indicate positions where arms were cloned in p2attNG derivatives). The GFP4m gene is a variant of EGFP (mut4EGFP) that exhibits improved folding at 37° C. (Okada A. et al., *Exp. Neurol.* 1999, 156, 394-406). E2A, equine rhinitis A virus 2A peptide; P2A, porcine teschovirus-1 2A peptide; T2A, Thosea asigna virus 2A peptide.

FIG. 3. Generation of recipient ESC and iPSC lines. (A) Genomic PCR was used to screen for clones that underwent correctly targeted spontaneous homologous recombination in H9 ESC, producing integration of the landing pad cassette at the H11 locus. A 3.6-kb band indicated correct targeting. (B) The TALEN pair used in this study to target the human H11 locus. The double-strand break was generated ~60-bp from the H11 locus. (C) Genomic PCR was used to screen for clones that underwent correctly targeted placement of the landing pad by TALEN-assisted homologous recombination in PI-1761 iPSC. Representative clones are shown, with the expected 1.1-kb band indicating correct placement.

Example 3: Characterization of ESC and iPSC Recipient Stem Cell Lines

Figure 4A:
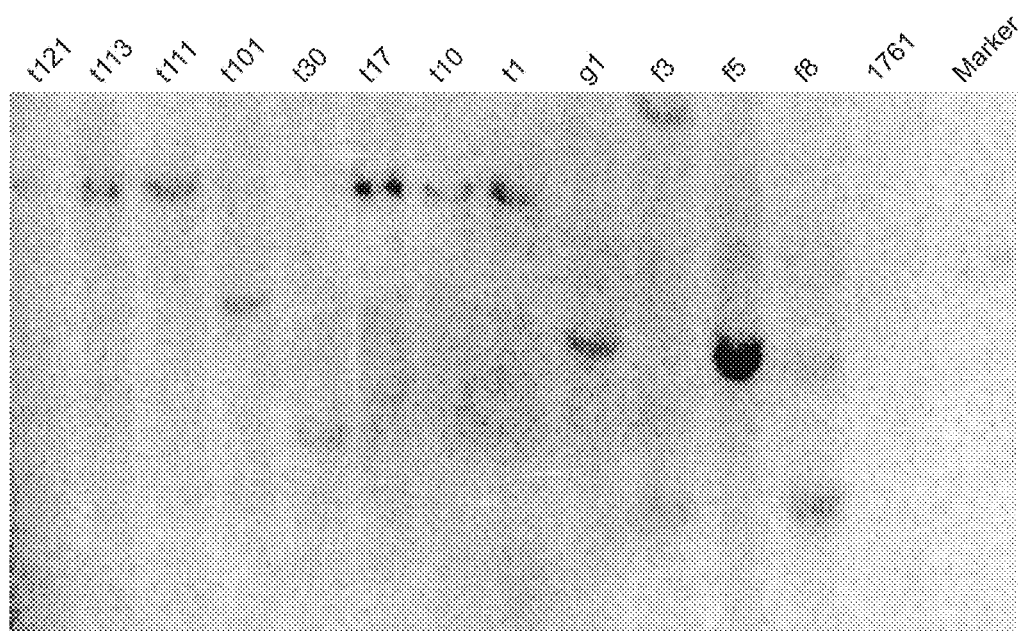
FIGS. 4A-4B show assays for copy numbers of transgenes in selected clones.
Figure 4B:
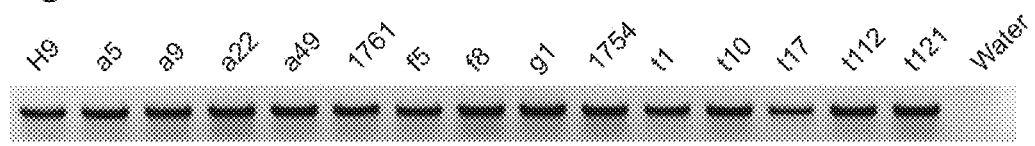
Figure 5A:
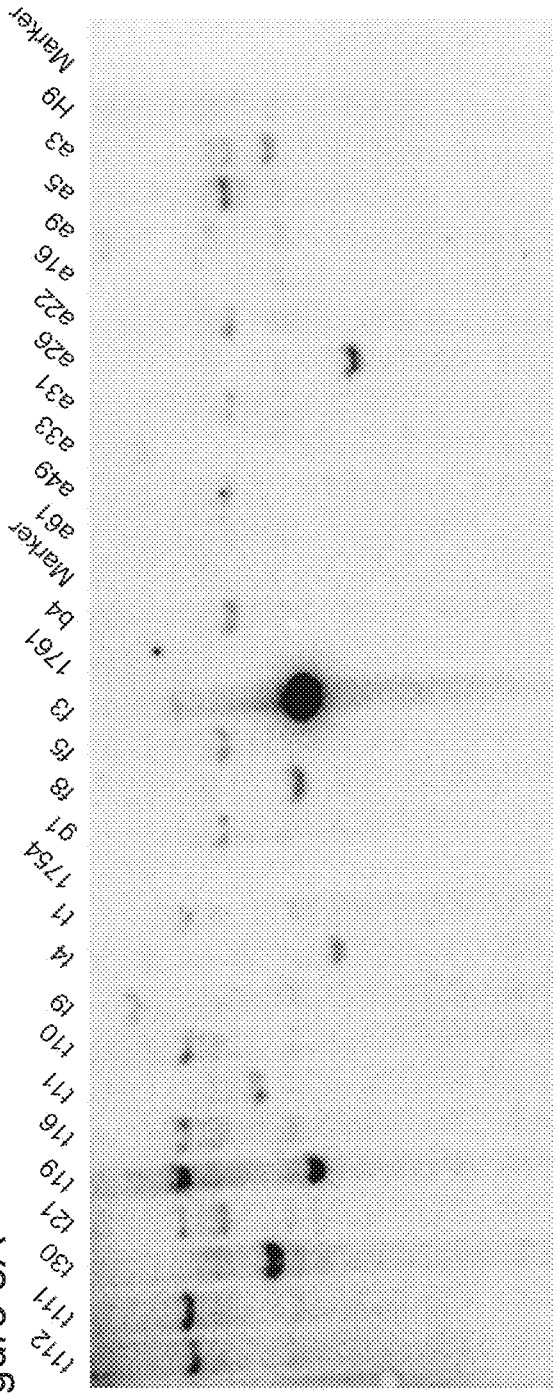
FIGS. 5A-5B show Southern blotting (FIG. 5A) and G-banding analysis (FIG. 5B) of recipient cell lines.

To identify ESC and iPSC recipient lines that have attP sites anchored at the H11 locus for use in further experiments, we first screened some of the correctly targeted clones for integration copy number by Southern blotting, using a probe directed to the GFP gene in the landing pad cassette (FIG. 1A). To determine whether one or both of the H11 alleles had been recombined, we performed genomic PCR using primers targeting regions around H11 in the human genome (FIG. 4B). The results showed that all clones tested that had been generated by spontaneous recombination had integrated a single copy of the landing pad, while some of the tested clones that resulted from TALEN-assisted recombination had integrated multiple copies (FIG. 5A, FIG. 4A). Some of the single-copy clones were sequenced to examine whether there were any mutations in the region, including the landing pad cassette and the homology arms. Mutations were detected in regions around the double-strand break in some of the clones derived from TALEN-assisted recombination. These results suggest that residual TALENs may have created additional double-strand breaks after the desired recombination event occurred, and NHEJ may have mediated DNA repair, generating these mutations. From the clones that were single-copy and mutation free, we randomly selected one clone for each cell line, namely a22 for H9, f5 for PI-1761, and t17 for PI-1754, for further characterization as candidates to become validated recipient cell lines.

Figure 6A:
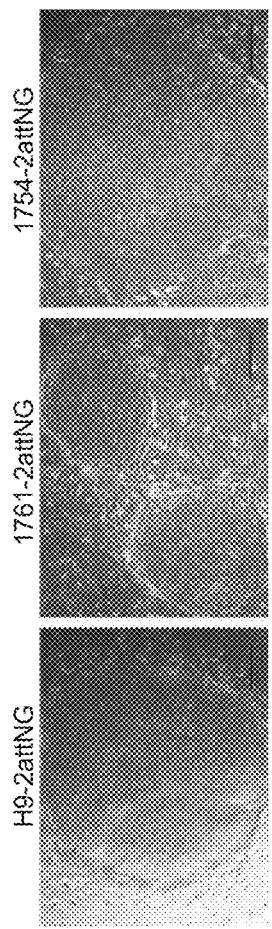
Figure 6B:
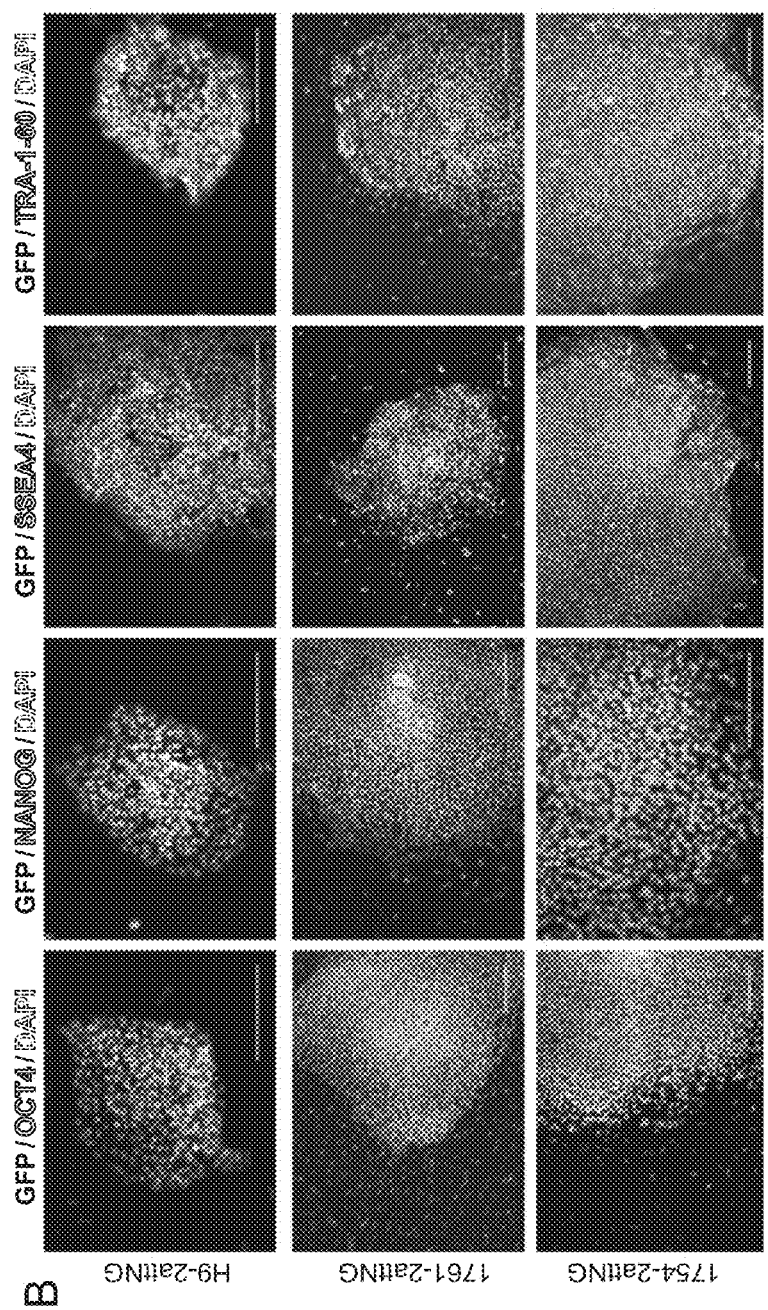

We tested whether these recipient lines, named H9-2attNG (a22), 1761-2attNG (f5), and 1754-2attNG (t17), remained pluripotent after genetic manipulation by immunostaining for pluripotency marker genes and by embryoid body (EB)-mediated in vitro differentiation. All three cell lines exhibited the typical morphology of pluripotent ESC and iPSC (FIG. 6A) and expressed GFP and a panel of pluripotency marker genes, including OCT3/4, SOX2, NANOG, SSEA4, and TRA-1-60 (FIG. 6B). After 16 days of in vitro differentiation, all lines generated cells positive for markers of the three germ layers, including alpha-fetoprotein (endoderm), alpha-smooth muscle actin (mesoderm), and beta III-tubulin (ectoderm) (FIG. 6C). Meanwhile, robust GFP expression was maintained in the three cell lines after extensive passaging (>30 passages) and after EB-mediated differentiation (FIG. 6C), suggesting robust expression from the H11 locus. Finally, G-banded karyotype analysis showed that all three recipient cell lines retained a normal karyotype (FIG. 6B).

In summary, recipient cell lines H9-2attNG ESC and 1761-2attNG and 1754-2attNG iPSC were successfully established, bearing phiC31 and Bxb1 integrase attP sites placed at the transcriptionally active H11 locus. Because these attP sites are recognized and actionable by the phiC31 and Bxb1 integrases, the recipient cell lines can be used to insert and express any genes of interest that are flanked by phiC31 and Bxb1 attB sites.

FIG. 4. Assays for copy numbers of transgenes in selected clones. (A) Southern blotting analysis for selected recipient cell lines. (B) Genomic PCR analysis for the second allele of the H11 locus showed that only one allele is targeted in all cell lines tested. "a" and "b" clones come from H9 targeted by spontaneous homologous recombination; "f" and "g" come from PI-1761 targeted by spontaneous homologous recombination; "t" clones come from PI-1754 targeted by TALEN-assisted homologous recombination.

Figure 5B:
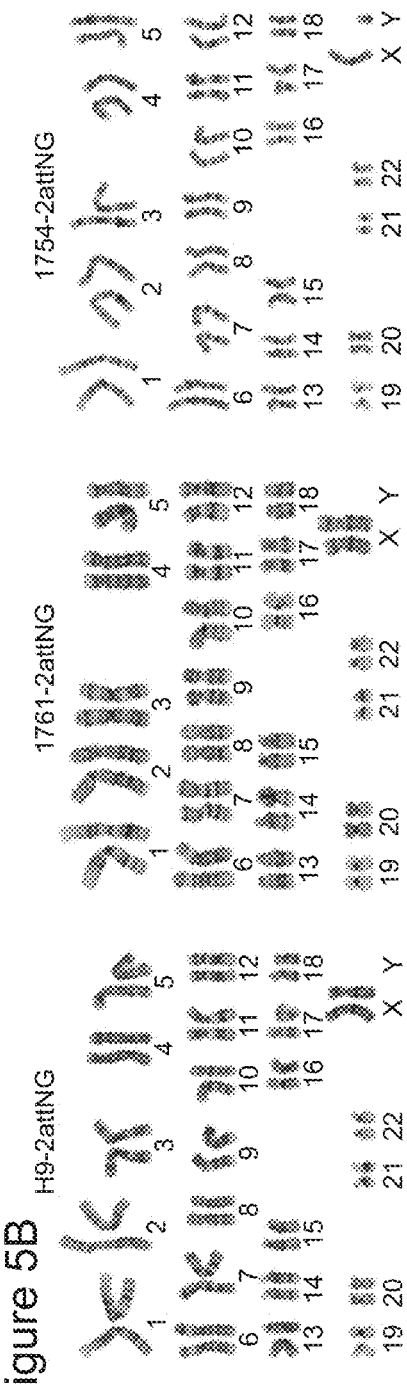

FIG. 5. Southern blotting and G-banding analysis of recipient cell lines. (A) Southern blot analysis of selected clones. Marker lanes refer to size markers, with 9.1-kb for spontaneous homologous recombination and 12.0-kb for TALEN-assisted homologous recombination. Clones given the 'a' and 'b' prefixes were from H9 ESC targeted by spontaneous homologous recombination, while 'f' and 'g' prefixes indicate clones derived from PI-1761 iPSC, also targeted by spontaneous homologous recombination. The t clones were from PI-1754 iPSC targeted by TALEN-assisted homologous recombination. (B) G-banding analysis of recipient cell lines, including H9 recipient cell line H9-2attNG (a22), PI-1761 recipient cell line 1761-2attNG (f5), and PI-1754 recipient cell line 1754-2attNG (t17).

FIG. 6. Pluripotency of recipient ESC and iPSC lines. (A) Typical ESC and iPSC morphology of the recipient cell lines H9-2attNG (left), 1761-2attNG (middle), and 1754-2attNG (right). (B) Immunostaining of pluripotency markers OCT3/4, NANOG, SSEA4, and TRA-1-60, for H9-2attNG (upper), 1761-2attNG (middle), and 1754-2attNG (lower). (C) Typical morphology of suspended EBs at day 8 (left) and immunostaining of marker genes for the three germ layers: AFP (endoderm), alpha-SMA (mesoderm), and Tuj1 (ectoderm) from H9-2attNG (upper), 1761-2attNG (middle), and 1754-2attNG (lower). Scale bar, 200 μm.

Example 4: Dual Integrase Cassette Exchange (DICE) in H9-2attNG

Figure 2B:
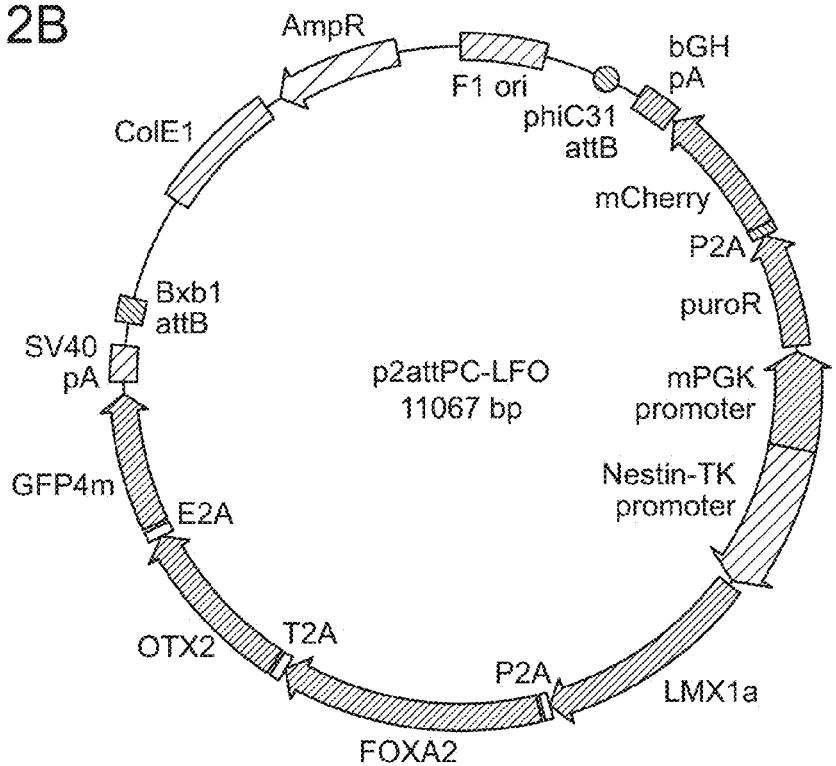
Figure 7A:
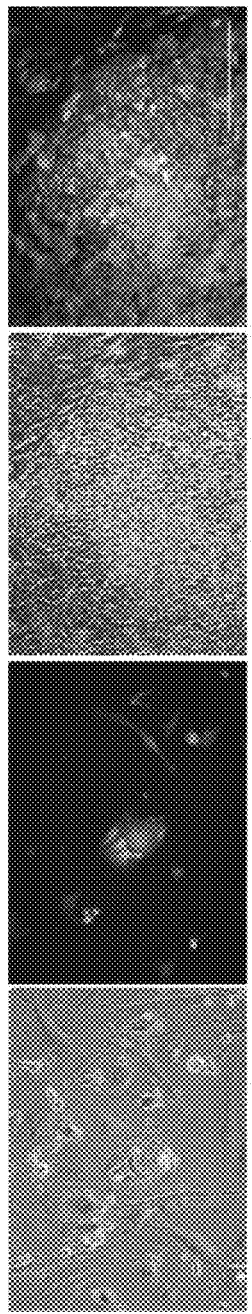
FIGS. 7A-7B show that DICE reaction is mediated by phiC31 and Bxb1 integrases.
Figure 7B:

A key feature of our strategy is that expression of phiC31 and Bxb1 integrases in recipient cell lines will catalyze site-specific, irreversible recombination between cognate attP and attB sites, resulting in precise replacement of the landing pad cassette by any donor cassette flanked by phiC31 and Bxb1 attB sites. We named this process dual integrase cassette exchange, abbreviated DICE (FIG. 1A). To determine the efficiency of DICE in a recipient cell line, we constructed a control donor vector in which phiC31 and Bxb1 attB sites flanked genes for the puromycin-resistance selection marker and the mCherry fluorescent marker protein, driven by the PGK promoter (FIG. 2B). We introduced this vector together with phiC31 and Bxb1 integrase expression vectors into the H9-2attNG recipient cell line by nucleofection, and started puromycin drug selection 3-5 days later, for 2-3 days. Within several days, the change in marker gene expression from GFP to mCherry was visible (FIG. 7A). After two weeks, twelve puro-resistant clones that were mCherry-positive and GFP-negative were picked at random. We tested whether DICE had occurred in these clones by performing genomic PCR using primers designed to detect the landing pad or donor cassettes. The results showed that all twelve of the clones (H9-PC) carried the puromycin-mCherry donor cassette at the H11 locus, while the landing pad cassette was no longer present. This result is consistent with DICE having successfully occurred in 100% of the picked clones (FIG. 7B, FIG. 8).

FIG. 7. DICE reaction mediated by phiC31 and Bxb1 integrases. (A) The visible change in marker gene expression as mCherry replaces GFP one and four days after nucleofection. (B) An example of genomic PCR for screening of correctly targeted clones after DICE, yielding a band of 1.2-kb. H9-LF (LMX1a-FOXA2) clones are shown. Scale bar, 200 μm.

Figure 8:
FIG. 8 illustrates analysis of DICE reaction.

FIG. 8. DICE analysis. An example of the genomic PCR carried out to screen for correctly targeted clones after DICE. Clones derived from 1754-2attNG are shown on this gel.

Example 5: Overexpression of Neural Transcription Factors in Recipient Stem Cell Lines We further asked whether the DICE genomic editing system could be employed as a rapid method to create cell lines that may be useful to optimize differentiation protocols into specific lineages by overexpressing relevant transcription factors. The transcription factors Lmx1a, FoxA2, and Otx2 were previously shown to be critical for dopaminergic neuron development in mouse (Chung, et al. (2009) Cell Stem Cell, 5, 646-658). Forced expression of these factors individually or in combinations in ESC improved neuronal differentiation (Chung et al., 2010, Brain, 133, 2022-2031; Friling et al., 2009, Proc Natl Acad Sci USA, 106, 7613-7618; Lin et al., 2009, Dev Biol., 333, 386-396). We hypothesized that overexpression of these factors specifically at the neural stem cell stage during directed differentiation from ESC or iPSC might be effective in increasing differentiation efficiency into dopaminergic neurons. To this end, we designed a series of four constructs, based on the control p2attPC donor vector, that carried the human LMX1a (L), FOXA2 (F), and OTX2 (0) coding sequences in all pairwise combinations and with all three together. GFP (G) was also included as a reporter, and the entire cassette was driven by the NESTIN enhancer and minimal thymidine kinase (TK) promoter. With this design, we expected that, at the stage of neuronal differentiation when the neural progenitor marker NESTIN is expressed, the inserted genes would be expressed as well.

We used ribosomal skipping 2A sequences, including 2A peptide regions from equine rhinitis A virus (ERAV, "E2A"), porcine teschovirus-1 (PTV-1, "P2A"), and insect Thosea asigna virus (TaV, "T2A"), to generate multicistronic vectors for efficient translation of the inserted genes (Szymczak et al. (2004) Nat. Biotechnol., 22, 589-594; Carey et al. (2009) Proc Natl Acad Sci USA, 106, 157-162) (FIG. 2B). 2A peptides have been reported to mediate stoichiometric production of separate proteins from dicistronic or multicitronic genes in multiple cell types (Szymczak et al., 2004, Nat. Biotechnol., 22, 589-594). The sizes of the transgene cassettes present between the two attB sites ranged from approximately 5-7 kb. We introduced phiC31 and Bxb1 integrase expression plasmids and each of the four different constructs into H9-2attNG and carried out similar nucleofection, selection, and analysis procedures to those described above. Genomic PCR analysis indicated that all clones (named H9-LFO, H9-LF, H9-LO, and H9-OF) tested had the desired donor cassette present at the H11 locus, whereas the original NG landing pad was no longer present, again indicating that DICE is 100% specific (FIG. 7B, Table 3).

Figure 11A:
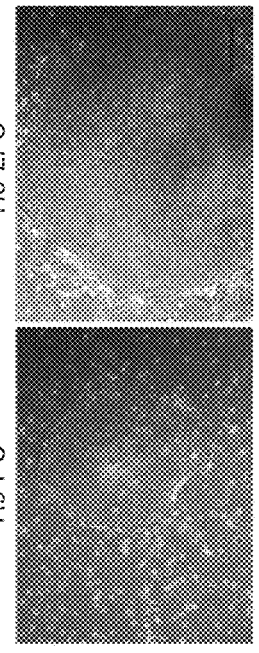
FIGS. 11A-11C show characterization of overexpression of neural transcription factors in correctly targeted clones.
Figure 11B:
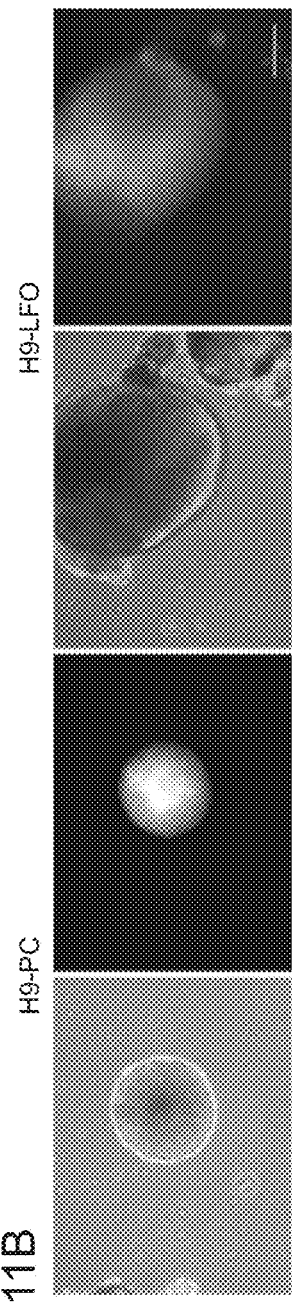

NESTIN in EB-differentiated cells by immunostaining and GFP by fluorescence (FIG. 11). NESTIN was turned on in some cells during EB-mediated differentiation, and these cells were also labeled by GFP expression, consistent with NESTIN-regulated expression of the transcription factor cassette. By contrast, no GFP-positive cells were detected in EB-differentiated cells from the control H9-PC (FIG. 11B).

Figure 11C:
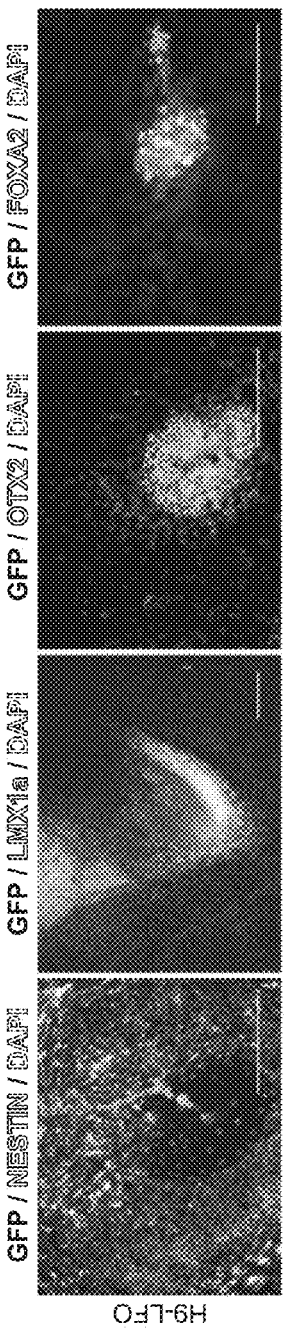

Immunostaining was then performed to examine the expression of the three transcription factors at day 16 of differentiation. The results showed that in differentiated cells from the H9-PC control line, only a few cells expressed FOXA2 and almost no cells expressed LMX1a or OTX2, reflecting the expected low endogenous expression pattern of these three transcription factors in randomly differentiated cells. However, in cells differentiated from the H9-LFO line, there were more cells expressing LMX1a, FOXA2, or OTX2, and most of these cells were also positive for GFP, suggesting that the expression of these introduced genes was activated by the exogenous NESTIN enhancer (FIG. 11C). Together these results suggested that ESC and iPSC genomes could be efficiently modified by the DICE method and that genes of interest could be faithfully expressed at the H11 locus, even after differentiation.

Figure 9:
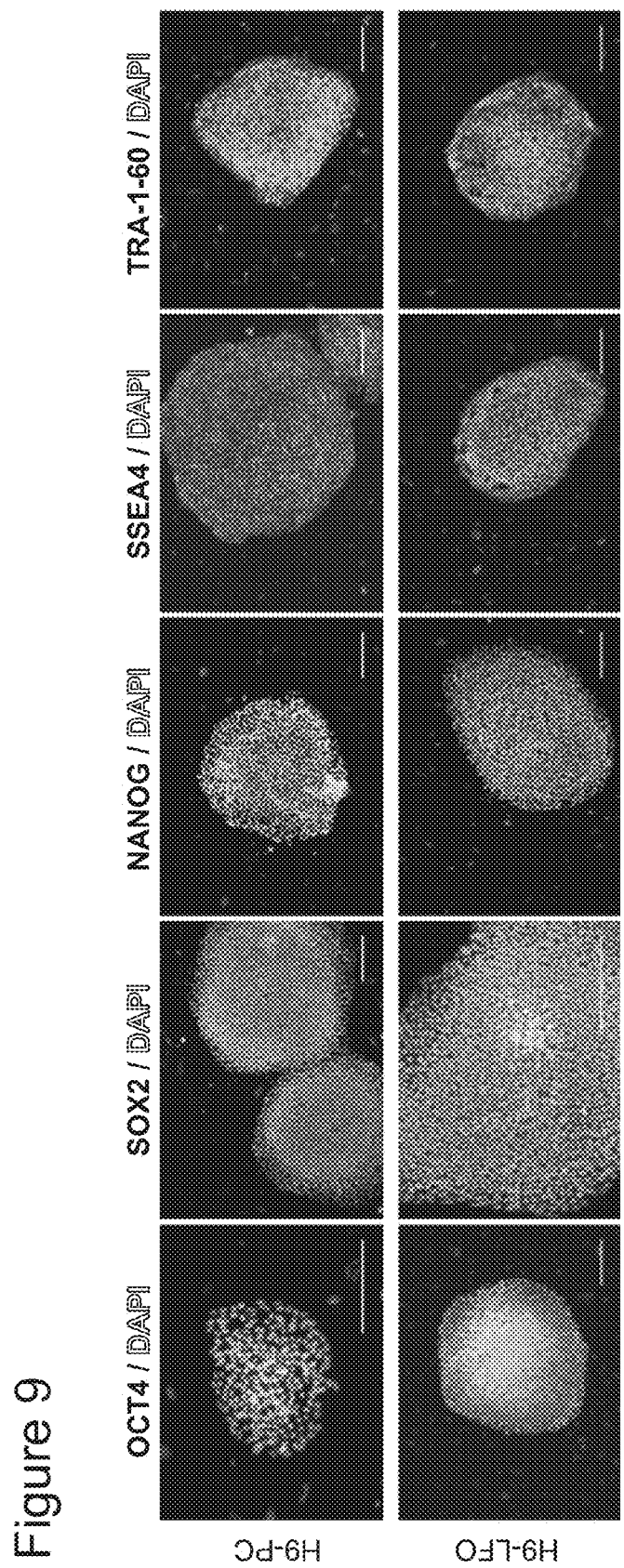
FIG. 9 depicts pluripotency analysis of clones via immunostaining.

FIG. 9. Pluripotency analysis. Immunostaining of pluripotency markers OCT3/4, SOX2, NANOG, SSEA4, and TRA-1-60, in H9-derived lines after DICE. H9-PC (upper) and H9-LFO (lower) are shown. Scale bar, 200 µm.

TABLE 3

Summary of DICE results in recipient ESC and iPSC lines. PC, puromycin-mCherry; L, LMX1a; F, FOXA2; O, OTX2. Correct addition of marker genes alone or marker and transcription factor genes occurred in 111/111 of the mCherry-positive, GFP-negative clones screened.

|  | PC positive clones/all clones | LFO positive clones/all clones | LO positive clones/all clones | LF positive clones/all clones | FO positive clones/all clones |
| --- | --- | --- | --- | --- | --- |
| H9-2attNg | 12/12 | 12/12 | 12/12 | 9/9 | 7/7 |
| 1761-2attNg | 17/17 | 11/11 | 7/7 | 3/3 | 5/5 |
| 1754-2attNg | 5/5 | 4/4 | 2/2 | 3/3 | 2/2 |

To determine whether DICE would also be effective in iPSC, we introduced the control p2attPC plasmid and each of the four transcription factor constructs into the 1761-2attNG and 1754-2attNG recipient iPSC lines. After co-transfection of phiC31 and Bxb1 integrase expression plasmids and the donor construct and puromycine selection, GFP-negative and mCherry-positive clones were picked randomly. Genomic PCR was used to detect which clones had undergone cassette exchange. Although fewer puromycin-resistant colonies were obtained from patient 1754 iPSC than from the normal sibling control 1761 iPSC, all of the randomly chosen clones were positive for the desired cassette exchange, as summarized in Table 3.

Figure 10:
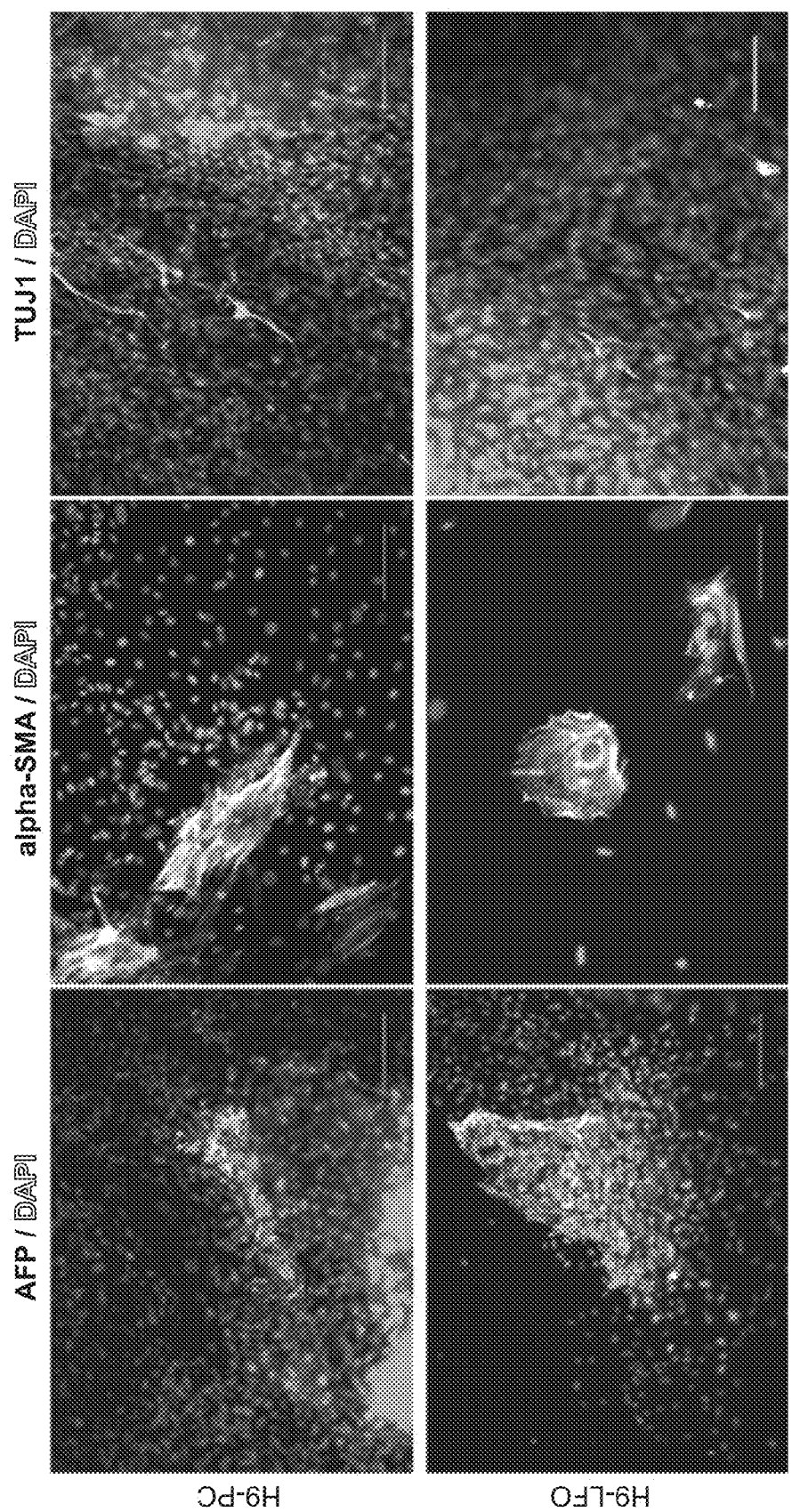
FIG. 10 shows immunostaining of markers for the three germ layers in H9-derived lines after DICE.

We then randomly chose two clones for further experiments representing H9-LFO, carrying LMX1a, FOXA2, OTX2, and GFP, and H9-PC, carrying only the puromycin and mCherry genes and no transcription factors. Both clones expressed a panel of typical pluripotentcy markers, including OCT3/4, NANOG, SSEA4, and TRA-1-60 (FIG. 9). Both clones also produced cells representative of the three germ layers after EB-mediated differentiation (FIG. 10). To determine whether the three transcription factors were overexpressed in a neuronal cell-specific manner in H9-LFO, we examined expression of the neuronal progenitor marker FIG. 10. Immunostaining of markers for the three germ layers in H9-derived lines after DICE: AFP (endoderm), alpha-SMA (mesoderm), and Tuj1 (ectoderm). H9-PC (upper) and H9-LFO (lower) are shown. Scale bar, 200 µm.

FIG. 11. Characterization of overexpression of neural transcription factors in correctly targeted clones. (A) Typical ESC morphology of H9 clones after DICE. H9-PC (control, left) and H9-LFO (LMX1a-FOXA2-OTX2, right) are shown. (B) The morphology of suspended EBs and the expression of mCherry and GFP at day 8 from H9-PC (left) and H9-LFO (right). (C) Immunostaining of NESTIN, LMX1a, OTX2 and FOXA2 in the H9-LFO line after 16 days of EB-mediated differentiation. Scale bar, 200 µm.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inserting a polynucleotide sequence into a genome of a human pluripotent stem cell, comprising:
   simultaneously introducing into the human pluripotent stem cell:
      a circular nucleic acid comprising the polynucleotide sequence flanked by a phiC31 first recombination site and a Bxb1 first recombination site;
      a phiC31 integrase; and
      a Bxb1 integrase,
   wherein the human pluripotent stem cell comprises a phiC31 second recombination site and a Bxb1 second recombination site at H11 locus in chromosome 22;
   maintaining the human pluripotent stem cell under conditions that facilitate simultaneous recombination between phiC31 first recombination and phiC31 second recombination sites and between the Bxb1 first recombination and Bxb1 second recombination sites,
   wherein the introducing and maintaining results in insertion of the polynucleotide sequence into the genome of the human pluripotent stem cell at the H11 locus an expression of a product of the polynucleotide sequence.

2. The method of claim 1, wherein the method comprises:
   inserting the phiC31 second recombination site and the Bxb1 second recombination site at the H11 locus prior to introducing the circular nucleic acid, and the phiC31 and Bxb1 integrases, wherein the inserting comprises:
      introducing into the human cell, a circular nucleic acid comprising the phiC31 second recombination site and the Bxb1 second recombination site flanked by a first sequence homologous to a first region of the H11 locus and a second sequence homologous to a second region of the H11 locus; and
      maintaining the human cell under conditions that facilitate recombination between the first sequence and the first region and between the second sequence and the second region,
   wherein the introducing and maintaining results in insertion of the phiC31 second recombination site and the Bxb1 second recombination site at the H11 locus.

3. The method of claim 1, wherein the phiC31 first recombination site is attB and the phiC31 second recombination site is attP.

4. The method of claim 1, wherein the phiC31 first recombination site is attP and the phiC31 second recombination site is attB.

5. The method of claim 1, wherein the Bxb1 first recombination site is attB and the Bxb1 second recombination site is attP.

6. The method of claim 1, wherein the Bxb1 first recombination site is attP and the Bxb1 second recombination site is attB.

7. The method of claim 1, wherein said phiC31 and Bxb1 integrases are introduced into the human cell by introducing a nucleic acid encoding the phiC31 and Bxb1 integrases into the cell.

8. The method of claim 1, wherein said phiC31 and Bxb1 integrases are introduced into the human cell by introducing a first nucleic acid encoding the phiC31 integrase and a second nucleic acid encoding the Bxb1 integrase.

9. The method of claim 7, wherein the nucleic acid is an mRNA.

10. The method of claim 7, wherein said nucleic acid is a circular DNA.

11. The method of claim 8, wherein the first and second nucleic acids are mRNA.

12. The method of claim 8, wherein the first and second nucleic acids are circular DNA.

13. The method of claim 1, wherein the polynucleotide encodes a polypeptide.

14. The method of claim 13, wherein the polypeptide is a transcription factor.

15. The method of claim 1, wherein the PS cell is an embryonic stem (ES) cell.

16. The method of claim 1, wherein the PS cell is an induced pluripotent stem (iPS) cell.

17. The method of claim 1, wherein the H11 locus is 4500-bp downstream of DRG1 and 683-bp downstream of EIF4ENIF1.

* * * * *